(12) United States Patent
Hausmanns et al.

(10) Patent No.: US 11,673,940 B2
(45) Date of Patent: Jun. 13, 2023

(54) RECOMBINANT PRODUCTION OF A COLLAGEN PEPTIDE PREPARATION AND USE THEREOF

(71) Applicant: Gelita AG, Eberbach (DE)

(72) Inventors: Stephan Hausmanns, Heidelberg (DE); Hans-Ulrich Frech, Weinheim (DE); Steffen Oesser, Glücksburg (DE); Martin Hahn, Gronau (DE)

(73) Assignee: Gelita AG, Eberbach (DE)

( * ) Notice: Subject to any disclaimer, the term of this patent is extended or adjusted under 35 U.S.C. 154(b) by 0 days.

(21) Appl. No.: 17/287,905

(22) PCT Filed: Nov. 6, 2019

(86) PCT No.: PCT/EP2019/080421
§ 371 (c)(1),
(2) Date: Apr. 22, 2021

(87) PCT Pub. No.: WO2020/094728
PCT Pub. Date: May 14, 2020

(65) Prior Publication Data
US 2021/0309723 A1    Oct. 7, 2021

(30) Foreign Application Priority Data

Nov. 6, 2018 (DE) ............. 10 2018 218 916.1
Jan. 23, 2019 (DE) ............. 10 2019 200 790.2
Feb. 26, 2019 (DE) ............. 10 2019 202 606.0

(51) Int. Cl.
| | | |
|---|---|---|
| C07K 14/78 | (2006.01) | |
| A61K 8/65 | (2006.01) | |
| A23L 33/18 | (2016.01) | |
| A61Q 3/00 | (2006.01) | |
| A61Q 5/00 | (2006.01) | |
| A61Q 19/00 | (2006.01) | |
| A61K 38/00 | (2006.01) | |

(52) U.S. Cl.
CPC .............. *C07K 14/78* (2013.01); *A23L 33/18* (2016.08); *A61K 8/65* (2013.01); *A61Q 3/00* (2013.01); *A61Q 5/00* (2013.01); *A61Q 19/00* (2013.01); *A23V 2002/00* (2013.01); *A61K 38/00* (2013.01)

(58) Field of Classification Search
CPC ............ C07K 14/78; A23L 33/18; A61K 8/65
See application file for complete search history.

(56) References Cited

U.S. PATENT DOCUMENTS

| | | | | |
|---|---|---|---|---|
| 5,593,859 A * | 1/1997 | Prockop | .......... | C12Y 114/11002 435/254.2 |
| 5,948,766 A | 9/1999 | Milan et al. | | |
| 2005/0229264 A1 * | 10/2005 | Chang | .............. | C08H 1/06 435/254.2 |
| 2006/0275345 A1 * | 12/2006 | Butzengeiger | ........... | A23L 33/28 424/439 |
| 2012/0245327 A1 * | 9/2012 | Nishio | ............... | C07K 14/78 530/356 |
| 2014/0073575 A1 * | 3/2014 | Hennet | ............... | C07K 14/78 514/17.2 |
| 2018/0319866 A1 * | 11/2018 | Elnajjar | ............... | C08H 1/06 |
| 2018/0344779 A1 * | 12/2018 | Petito | .................. | A61K 47/42 |

FOREIGN PATENT DOCUMENTS

| | | |
|---|---|---|
| DE | 102012110612 A1 | 5/2014 |
| WO | 20010034646 A2 | 5/2001 |
| WO | 20010034801 A2 | 5/2001 |
| WO | 2012065782 A2 | 5/2012 |
| WO | 2012117012 A1 | 9/2012 |
| WO | 2014072235 A1 | 5/2014 |

OTHER PUBLICATIONS

Khiari et al., 2014, Low molecular weight bioactive peptides derived from the enzymatic hydrolysis of collagen after isoelectric solubilization/precipitation process of turkey by-product, Poultry Science, 93: 2347-2362.*
Pihlajaniemi et al., 1987, Partial characterization of a low molecular weight human collagen that undergoes alternative splicing, PNAS, 84: 940-944.*
Sibilla et al., 2015, An Overview of the Beneficial Effects of Hydrolysed Collagen as a Nutraceutical on Skin Properties: Scientific Background and Clinical Studies, The Open Nutraceutical Journal, 8: 29-42.*
Aggarwal et al., 2008, Fibroblast Activation Protein Peptide Substrates Identified from Human Collagen I Derived Gelatin Cleavage Sites, Biochemistry, 47(3): 1076-1086.*
Olsen et al., 2003, Recombinant collagen and gelatin for drug delivery, Advanced Drug Delivery Reviews, 55: 1547-1567.*
Toman et al., 2000, Production of Recombinant Human Type I Procollagen Trimers Using a Four-gene Expression System in the Yeast *Saccharomyces cerevisiae*, 275(30): 23303-23309.*
Juher et al., 2015, An Overview of the Beneficial Effects of Hydrolysed Collagen Intake on Joint and Bone Health and on Skin Ageing, Nutr Hosp, 32(Supl 1): 62-66.*
Vuorela et al., 1997, Assembly of human prolyl 4-hydroxylase and type III collagen in the yeast *Pichia pastoris*: formation of a stable enzyme tetramer requires coexpression with collagen and assembly of a stable collagen requires coexpression with prolyl 4-hydroxylase, The EMBO Journal, 16(22): 6702-6712.*
Mazzorana et al., 1996, Involvement of Prolyl 4-Hydroxylase in the Assembly of Trimeric Minicollagen XII, The Journal of Biological Chemistry, 271(46): 29003-29008.*

(Continued)

*Primary Examiner* — Amber D Steele
(74) *Attorney, Agent, or Firm* — Sheppard Mullin Richter & Hampton LLP

(57) ABSTRACT

The present invention relates to a method for producing collagen peptide preparations comprising recombinant collagen peptides, to collagen peptide preparations produced by means of said methods, to products containing the collagen peptide preparations and to uses of the aforementioned preparations and products.

13 Claims, 10 Drawing Sheets

(56) References Cited

OTHER PUBLICATIONS

Wagner et al., 2000, Coexpression of alpha and beta subunits of prolyl 4-hydroxylase stabilizes the triple helix of recombinant human type X collagen, Biochem J, 352: 907-911.*

Xu et al., 2011, Hydroxylation of recombinant human collagen type I alpha 1 in transgenic maize co-expressed with a recombinant human prolyl 4-hydroxylase, BMC Biochemistry, 11:69 (12 pages).*

Geerlings et al., "A Novel Platform for the Production of Nonhydroxylated Gelatin Based on the Methylotrophic Yeast *Hansenula polymorpha*", FEMS Yeast Res, Jul. 26, 2007, pp. 1188-1196.

International Search Report (English translation) and Written Opinion for PCT/EP2019/080421 dated Jan. 10, 2020, 13 pages.

Kivirikko et al., "Further Hydroxylation of Lysyl Residues in Collagen by Protocollagen Lysyl Hydroxylase in Vitro", Biochemistry, vol. 12, No. 24, 1973, pp. 4966-4971.

Olsen et al., "Expression and Characterization of a Low Molecular Weight Recombinant Human Gelatin: Development of a Substitute for Animal-derived Gelatin with Superior Features", Protein Expression and Purification, vol. 40, No. 2, Apr. 1, 2005, pp. 346-357.

Response to Third Party Observation for PCT/EP2019/080421 dated Mar. 25, 2021, 8 pages.

Third Party Observation for PCT/EP2019/080421 dated Nov. 25, 2020, 27 pages.

Utroske, Geltor Shows Bio-tech Collagen at In-cosmetics North America, URL:https:/www.cosmeticsdesign.com/Article/2018/10/25/Geltor-shows-bio-tech-collagen-at-in-cosmetics-North-America, retrieved Oct. 25, 2018, 2 pages.

Wang et al., "Production of Recombinant Collagen: State of the Art and Challenges", Engineering Biology, The Institution of Engineering and Technology, vol. 1, No. 1, Jun. 1, 2017, pp. 18-23.

* cited by examiner

RECOMBINANT PRODUCTION OF A COLLAGEN PEPTIDE PREPARATION AND USE THEREOF

CROSS REFERENCE TO RELATED APPLICATIONS

This application is a U.S. National Stage Application under 35 U.S.C. 371 of International Application No. PCT/EP2019/080421, filed Nov. 6, 2019, which claims priority to German Patent Applications 10 2018 218 916.1, filed Nov. 6, 2018, 10 2019 200 790.2, filed Jan. 23, 2019, and 10 2019 202 606.0, filed Feb. 26, 2019. The contents of each of the aforementioned are hereby incorporated by reference in their entirety into the present disclosure.

The present invention relates to methods for producing collagen peptide preparations containing recombinant collagen peptides, the collagen peptide preparations produced by means of these methods, products containing the collagen peptide preparations and uses of the aforementioned preparations and products.

Collagen is an extracellular structural protein found in animals, for example, in mammals, birds, and fish. It is usually found there in the connective tissue, in particular, as part of the extracellular matrix. Tendons, ligaments, cartilage and bones are particularly rich in collagen. However, collagens are not found in plants and single-celled organisms.

Collagens occur in different, structurally and functionally different types and differ in terms of their structure, function and origin, among other things. The polypeptide chains that make up collagen are individually synthesized in the cell on the ribosomes of the endoplasmic reticulum in the form of larger precursor molecules and have extensive repetitive $(Gly-X-Y)_n$ sequences, where X and Y may be any amino acid, but usually proline and 4-hydroxyproline.

These precursor polypeptide chains are post-translationally hydroxylated on proline and lysine residues of the polypeptide chain in the endoplasmic reticulum while forming hydroxyproline and hydroxylysine residues. The hydroxylation serves to stabilize neighboring collagen polypeptide chains of the right-handed triple helix that forms in the cell, each made up of three of the precursor polypeptide chains (procollagen).

The procollagen thus formed is glycosylated intracellularly, secreted by the cell in the glycosylated triple-helical form (tropocollagen) and collagen is subsequently formed by peptidase-mediated cleavage of the terminal residues. In the course of a fibrillogenesis process, this accumulates to form collagen fibrils, which are then covalentiy cross-linked to form collagen fibers.

Collagen is often used in denatured form, then known as gelatin, or in the form of hydrolyzates.

If gelatin and collagen are subjected to hydrolytic processes, in particular enzymatic hydrolysis, collagen hydrolysates having a wide variety of compositions and application profiles may be produced, depending on the type of collagen used and the origin and the enzymatic conditions. These collagen hydrolysates represent a mixture of peptides, the molecular weights of which are distributed over certain size ranges. The use of such collagen hydrolyzates, for example, as food supplements or as cosmetic auxiliaries, has been known for a long time, among other things, for the prevention and/or treatment of complaints that are related to the bones, the joints or to the connective tissue.

Thus, WO 2012/065782 describes collagen hydrolysates obtained from pork rind gelatin, which are used to stimulate the biosynthesis of extracellular matrix proteins by skin cells and are particularly suitable for cosmetic purposes.

WO 2012/117012 discloses enzymatically hydrolyzed collagen from bovine split with an average molecular weight of 1500 to 8000 Da, which may be used together with a prebiotic for the prevention and/or treatment of osteoporosis.

Although the use of collagen hydrolysates obtained from animal materials has advantages for many applications and consumer groups, the use of collagen hydrolysates obtained in this way may also be less desirable with a view to certain consumer groups and application profiles. Certain consumer groups are fundamentally critical of or opposed to raw materials obtained from animal materials, be it that contamination including microorganisms or agents harmful to health, for example, process auxiliaries, or unwanted immune reactions are feared, or for religious or ethical reasons. In addition, the manufacturing processes used to obtain collagen hydrolyzates obtained from animal materials often include complex and expensive development, purification and further processing steps. Finally, it may be useful for certain applications to provide a collagen hydrolyzate that is standardized, precisely and reliably defined with regard to its origin and composition, which collagen hydrolyzate may advantageously also be produced inexpensively on an industrial scale.

Against this background, it is not surprising that methods have been developed for producing gelatin and collagen as well as hydrolysates thereof using recombinant genetic engineering.

Thus, WO 2006/052451 A2 discloses the production of recombinant type III collagen in *Pichia pastoris* strains which also express human prolyl hydroxylases.

WO 2005/012356 A2 discloses the production of gelatin from human collagen type I and individual 50 kDa, 65 kDa and 100 kDa collagen peptide species, each in completely hydroxylated, partially and non-hydroxylated form.

WO 01/34646 A2 likewise discloses the production of individual recombinant gelatin species, each with a defined molecular weight resulting from the recombinant production route, which may be present in non-hydroxylated, partially or completely hydroxylated form.

However, the production of recombinant collagen or hydrolyzates thereof, which are characterized by structural and functional properties that are the same or at least similar to those of collagen or collagen hydrolyzates obtained from natural sources, is problematic. This is partly because the natural formation of collagen is a comparatively complex physiological process, characterized by a number of intra- and extracellular influencing factors, which also includes post-translational synthesis steps, such as glycosylation and hydroxylation. These post-translational synthesis steps, in particular the specific positioning and the extent of the hydroxylation of proline and lysine, ensure the provision of stable tropocollagen, which ultimately associates to form fibrils and fibers. Thus, from Wang et al. (Engineering Biology, 2017 (1), 18-23) it is known that the current recombinant production of collagen is characterized by low yields, high costs and, in particular, by missing or deviating post-translational synthesis steps as they occur in the formation of native collagen. It is also known that precisely these post-translational modifications are essential for both the natural structure and function of collagen and for applications using collagen or collagen hydrolysates.

Accordingly, to date no recombinantly produced collagens or collagen hydrolyzates are known that have a structure, in particular the quality and quantity of post-translational modifications, in particular the degrees of hydroxylation and glycosylation and the hydroxylation and glycosylation positions, which is identical to natural collagen or to collagen hydrolyzates obtained therefrom.

The provision of recombinantly produced collagen and collagen hydrolysates with a property potential specifically derived from conventionally produced collagen or collagen hydrolysates is not readily possible, among other reasons, due to the circumstances described above, in particular the differences in the starting materials and production methods. In prokaryotic organisms, in particular, which are suitable per se for the industrial production of recombinant proteins, the production of recombinant collagen is problematic among other reasons in that, as a rule, the post-translational synthesis steps must also be introduced into the cell using recombinant technologies and this results in an additional metabolic load, which makes the expression and production of the desired collagen peptides difficult or impossible. In addition, the expression of foreign proteins may be toxic to the host cell, the recovery of recombinantly produced proteins in or from host cells may prove to be technically or economically unfeasible, the stability of the expression product obtained may be too low, or other effects such as growth and reproductive disorders of the host cell may occur.

There is therefore still a great need to provide recombinantly produced collagen hydrolyzates for applications in a wide variety of areas, in particular also for therapeutic purposes, in particular for the prophylaxis or treatment of conditions or diseases affecting the muscles, joints, bones and skin of humans and animals.

The present invention is therefore based on the technical problem of providing methods for the production of collagen peptide preparations and the recombinant collagen peptide preparations thus obtained, which overcome the aforementioned disadvantages, in particular, which may be produced recombinantly in a standardized, reliable and precisely defined form, also on a larger industrial and cost-effective scale, and which exhibit in particular improved properties, in particular effectiveness comparable to corresponding collagen hydrolysates obtained from animal materials, in particular develop biological effectiveness with regard to maintaining the health of muscles, joints, bones and skin and in the prophylaxis or treatment of diseases that affect the muscles, joints, bones and skin of humans and animals.

The present invention solves the technical problem underlying it by providing the teachings of the independent claims, in particular, also the teachings of the preferred embodiments in the description and in the dependent claims.

The present invention relates, in particular, to a method for producing a collagen peptide preparation containing recombinant collagen peptides, comprising the method steps
a) providing an expression system, which includes at least one expression cassette, the expression cassette including at least one nucleotide sequence that encodes a collagen peptide having a molecular weight in a range from 8 to 100 kDa,
b) incubating the expression system under conditions that allow expression of the collagen peptide,
c) obtaining the collagen peptide,
d) hydrolyzing the collagen peptide under conditions that result in the production of a collagen peptide preparation, which includes collagen peptides having an average molecular weight of 1 to 7 kDa and a molecular weight in a range of 0.1 to 13.5 kDa and
e) obtaining the collagen peptide preparation.

The method provided according to the invention for the production of collagen peptide preparations is characterized, in particular, by the fact that a recombinantly produced collagen peptide preparation is provided by hydrolysis from at least one, preferably precisely defined, recombinantly produced collagen peptide of a specific size from 8 to 100 kDa, which has a molecular weight distribution and structure which advantageously result from the recombinant specific collagen peptide species used for the hydrolysis and from the subsequent method steps, in particular the hydrolysis step, in particular the hydroxylation profile, and which, despite its recombinant production, is characterized by an advantageous biological activity directly and without further preparation steps.

The collagen peptide preparations provided according to the invention exhibit significant differences in their structure due to their recombinant production method, in particular, with regard to the modifications introduced by post-translational synthesis steps, such as hydroxylations and glycosylations, to collagen hydrolysates obtained from natural sources. Surprisingly, they may be provided in a wide variety of expression systems, even on an industrial scale, without undesired contamination, while at the same time having advantageous biological effectiveness, in particular, with regard to applications for maintaining and improving the health of bones, cartilage, skin, hair and nails.

The biological effectiveness of the recombinant collagen peptide preparations provided here, found according to the invention, already applies to the preparations obtained directly from the hydrolysis, without the need for further processing steps.

The biological effectiveness found according to the invention and the recombinantly produced collagen peptide preparations of the present invention may be determined in particular using in vitro tests to stimulate the synthesis of extracellular matrix proteins in osteoblasts, fibroblasts and chondrocytes, preferably using in vitro tests to stimulate the synthesis of extracellular matrix proteins or mRNA coding for these proteins in osteoblasts, fibroblasts and chondrocytes, in particular using the in vitro tests shown in Examples 3 to 7, in particular Examples 3 to 5, for stimulating the synthesis of extracellular matrix proteins in osteoblasts, fibroblasts and chondrocytes.

In one preferred embodiment, the recombinant collagen peptide-containing collagen peptide preparations of the present invention produced according to the invention exhibit a biological activity in at least one in vitro test for stimulating the synthesis of extracellular matrix proteins in osteoblasts, fibroblasts and chondrocytes, in particular in at least one, preferably at least two, preferably in all of the in vitro tests for stimulating the synthesis of extracellular matrix proteins in osteoblasts, fibroblasts and chondrocytes shown in Examples 3 to 7, in particular, in Examples 3 to 5.

The recombinant collagen peptide-containing collagen peptide preparations of the present invention produced according to the invention exhibit in at least one in vitro test for stimulating the synthesis of extracellular matrix proteins in osteoblasts, fibroblasts and chondrocytes, in particular in at least one, preferably in at least two, preferably in all of the in vitro tests for stimulating the synthesis of extracellular matrix proteins in osteoblasts, fibroblasts and chondrocytes shown in Examples 3 to 7, in particular, in Examples 3 to 5, the same biological effectiveness as collagen peptide preparations isolated from natural sources, in particular, non-recombinantly produced collagen peptide preparations.

The recombinant collagen peptide-containing collagen peptide preparations of the present invention produced according to the invention particularly preferably exhibit in at least one in vitro test for stimulating the synthesis of extracellular matrix proteins in osteoblasts, fibroblasts and chondrocytes, in particular in at least one, preferably in at least two, preferably in all of the in vitro tests for stimulating the synthesis of extracellular matrix proteins in osteoblasts, fibroblasts and chondrocytes shown in Examples 3 to 7, in particular, in Examples 3 to 5, a better biological effectiveness than collagen peptide preparations isolated from natural sources, in particular, non-recombinantly produced collagen peptide preparations.

In one preferred embodiment of the present invention, the expression system provided in step a) is a cell-based or cell-free expression system.

The expression system provided in step a), in particular the cell-based expression system, is preferably a host cell, in particular a prokaryotic or eukaryotic cell.

The expression system, in particular the cell-based expression system, is preferably a host cell selected from the group made up of bacterial cells, yeast cells, fungal cells, mammalian cells, insect cells and plant cells.

The expression system, in particular the cell-based expression system, is preferably a bacterial cell, in particular, of the species *Escherichia coli* or *Bacillus subtilis*.

In a further preferred embodiment, the expression system, in particular the cell-based expression system, is a yeast cell, in particular of the species *Saccharomyces cerevisiae, Pichia pastoris* or *Ogataea angusta* (*Hansenula polymorpha*).

The expression system, in particular the cell-based expression system, is preferably a fungal cell, in particular of the *Aspergillus niger* species.

In a further preferred embodiment of the present invention, the expression system, in particular the cell-based expression system, is a mammalian cell, in particular a CHO cell, a HeLa cell or a HEK293 cell.

The expression system, in particular the cell-based expression system, is preferably an insect cell, in particular an Sf-9, Sf-21 or Tn-5 cell.

The expression system, in particular the cell-based expression system, is preferably a plant cell, in particular a maize or tobacco cell.

In a further preferred embodiment of the present invention, the expression system provided in step a) is an expression system, in particular a cell-based expression system, which is capable of hydroxylating proline residues, lysine residues or proline residues and lysine residues of the expressed collagen peptide. The expression system provided in step a) is preferably a host cell which is capable of hydroxylating proline residues, lysine residues or proline residues and lysine residues of the expressed collagen peptide.

The expression system provided in step a) is preferably an expression system, in particular a cell-based expression system, which exhibits prolyl hydroxylase activity and/or lysyl hydroxylase activity. The expression system provided in step a) is preferably a host cell which exhibits prolyl hydroxylase activity and/or lysyl hydroxylase activity.

In one preferred embodiment, the expression system provided in step a) is a cell-based expression system including at least one expression cassette which comprises a prolyl 4-hydroxylase-encoding polynucleotide sequence. The expression system provided in step a) is particularly preferably a cell-based expression system including at least one expression cassette which comprises a prolyl 4-hydroxylase-encoding polynucleotide sequence, so that an in vivo hydroxylated collagen peptide preparation is obtained in method step e).

In one preferred embodiment, the expression system provided in step a) is a cell-based expression system including at least one expression cassette which comprises a lysyl hydroxylase-encoding polynucleotide sequence. The expression system provided in step a) is particularly preferably a cell-based expression system including at least one expression cassette which comprises a lysyl hydroxylase-encoding polynucleotide sequence, so that an in vivo hydroxylated collagen peptide preparation is obtained in method step e).

In a further preferred embodiment of the present invention, the expression system provided in step a) is a cell-based expression system including at least one expression cassette which comprises a prolyl-4-hydroxylase-encoding polynucleotide sequence and at least one expression cassette which comprises a lysyl hydroxylase-encoding polynucleotide sequence. The expression system provided in step a) is particularly preferably a cell-based expression system including at least one expression cassette which comprises a prolyl-4-hydroxylase-encoding polynucleotide sequence and at least one expression cassette which comprises a lysyl hydroxylase-encoding polynucleotide sequence, so that in method step e) an in vivo hydroxylated collagen peptide preparation is obtained.

Accordingly, the present invention also comprises a method for producing a collagen peptide preparation containing recombinant collagen peptides, in particular, an in vivo hydroxylated collagen peptide preparation, comprising the method steps a) providing a cell-based expression system that includes at least one expression cassette, wherein the expression cassette includes at least one nucleotide sequence which encodes a collagen peptide having a molecular weight in a range from 8 to 100 kDa and wherein the cell-based expression system is capable of hydroxylating proline residues, lysine residues or proline and lysine residues of the expressed collagen peptide, b) incubating the expression system, in particular cultivating the cell-based expression system, under conditions which enable the expression and hydroxylation of the collagen peptide, c) obtaining the collagen peptide, in particular the in vivo hydroxylated collagen peptide, d) hydrolyzing the collagen peptide, in particular the in vivo hydroxylated collagen peptide, under conditions which result in the production of a collagen peptide preparation, the collagen peptides, in particular in vitro hydroxylated collagen peptides, having an average molecular weight of 1 to 7 kDa and a molecular weight in a range from 0.1 to 13.5 kDa and e) obtaining the collagen peptide preparation, in particular the in vivo hydroxylated collagen peptide preparation, hereinafter also referred to as collagen peptide preparation A.

With the aid of the aforementioned method, it is thus advantageously possible to obtain a collagen preparation with in vivo hydroxylated recombinantly produced collagen peptides having a specific molecular weight and a specific average molecular weight, which, depending on the cell-based expression system used, is characterized by a specific pattern of post-translational modifications, in particular hydroxylations and glycosylations. In this way, it is advantageously possible, in particular, to obtain a collagen peptide preparation having biological effectiveness directly, i.e., without the need for subsequent modification of the collagen peptides of the collagen peptide preparation.

In a preferred embodiment, the in vivo hydroxylated collagen peptide preparation containing the recombinant collagen peptides produced according to the invention, i.e., collagen peptide preparation A, exhibits a biological activity in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes.

The in vivo hydroxylated collagen peptide preparation containing the recombinant collagen peptides produced according to the invention, i.e., collagen peptide preparation A, preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, the same biological effectiveness as collagen peptide preparations isolated from natural sources, in particular non-recombinantly produced collagen peptide preparations.

The in vivo hydroxylated collagen peptide preparation containing the recombinant collagen peptides produced according to the invention, i.e., collagen peptide preparation A, particularly preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, a better biological effectiveness than collagen peptide preparations isolated from natural sources, in particular non-recombinantly produced collagen peptide preparations.

According to a further embodiment of the present invention, the expression system provided in step a) is an expression system which is not capable of bringing about a hydroxylation of proline residues, lysine residues or proline and lysine residues of the expressed collagen peptide, in particular, the expression system provided in step a) does not exhibit prolyl hydroxylase activity and lysyl hydroxylase activity.

The present invention thus comprises a method for producing a recombinant collagen peptide-containing collagen peptide preparation, in particular a non-hydroxylated collagen peptide preparation, comprising the method steps
a) providing an expression system including at least one expression cassette, wherein the expression cassette includes at least one nucleotide sequence which encodes a collagen peptide having a molecular weight in a range of 8 to 100 kDa and wherein the expression system is not capable of hydroxylating proline residues, lysine residues or proline and lysine residues of the expressed collagen peptide,
b) incubating the expression system under conditions that allow expression of the collagen peptide,
c) obtaining the collagen peptide, especially the non-hydroxylated collagen peptide,
d) hydrolyzing the collagen peptide, in particular the non-hydroxylated collagen peptide, under conditions which result in the production of a collagen peptide preparation including collagen peptides having an average molecular weight of 1 to 7 kDa and a molecular weight in a range from 0.1 to 13.5 kDa and
e) obtaining the collagen peptide preparation, in particular the non-hydroxylated collagen peptide, also referred to below as collagen peptide preparation B.

In a preferred embodiment, the non-hydroxylated collagen peptide preparation containing the recombinant collagen peptides produced according to the invention, i.e., collagen peptide preparation B, exhibits a biological activity in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes.

Preferably, the non-hydroxylated collagen peptide preparation containing recombinant collagen peptides produced according to the invention, i.e., collagen peptide preparation B, exhibits in at least one in vitro test for stimulating the synthesis of extracellular matrix proteins in osteoblasts, fibroblasts and chondrocytes, in particular in at least one, preferably in at least two. preferably in all of the in vitro tests shown in Examples 3 to 7, in particular Examples 3 to 5, for stimulating the synthesis of extracellular matrix proteins in osteoblasts, fibroblasts and chondrocytes, the same biological effectiveness as collagen peptide preparations isolated from natural sources, in particular non-recombinantly produced collagen peptide preparations.

The non-hydroxylated collagen peptide preparation containing recombinant collagen peptides produced according to the invention, i.e., collagen peptide preparation B, particularly preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, a better biological effectiveness than collagen peptide preparations isolated from natural sources, in particular non-recombinantly produced collagen peptide preparations.

In one preferred embodiment of the present invention, the collagen peptide obtained in method step c) is hydroxylated in a method step x1) before carrying out method step d) and a pre-lysal, i.e. prior to hydrolysis, ex vivo hydroxylated collagen peptide preparation is obtained in method step e).

Accordingly, the present invention further comprises a method for producing a collagen peptide preparation containing recombinant collagen peptides, in particular a collagen peptide preparation which is pre-lysally hydroxylated ex vivo, comprising the method steps
a) providing an expression system including at least one expression cassette, wherein the expression cassette includes at least one nucleotide sequence that encodes a collagen peptide having a molecular weight in a range of 8 to 100 kDa and wherein the expression system is not capable of hydroxylating proline residues, lysine residues or proline and lysine residues of the expressed collagen peptide,
b) incubating the expression system under conditions that allow expression of the collagen peptide,
c) obtaining the collagen peptide,
x1) ex vivo hydroxylation of the collagen peptide obtained in step c), d) hydrolyzing the collagen peptide, in particular the ex vivo hydroxylated collagen peptide, under conditions which result in the production of a collagen peptide preparation that includes collagen peptides, in particular ex vivo hydroxylated collagen peptides, of an average molecular weight of 1 to 7 kDa and having a molecular weight in a range from 0.1 to 13.5 kDa and e) obtaining the collagen peptide preparation, in particular the pre-lysally ex vivo hydroxylated collagen peptide preparation, hereinafter also referred to as collagen peptide preparation C.

In a preferred embodiment, the pre-lysally ex vivo hydroxylated collagen peptide preparation containing recombinant collagen peptides produced according to the invention, i.e., collagen peptide preparation C, exhibits a biological activity in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes.

The recombinant collagen peptide containing pre-lysally ex vivo hydroxylated collagen peptide preparation prepared according to the invention, i.e., collagen peptide preparation C, preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, the same biological effectiveness as collagen peptide preparations isolated from natural sources, in particular non-recombinantly produced collagen peptide preparations.

The pre-lysally ex vivo hydroxylated collagen peptide preparation containing recombinant collagen peptides produced according to the invention, i.e., collagen peptide preparation C, particularly preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, a better biological effectiveness than collagen peptide preparations isolated from natural sources, in particular non-recombinantly produced collagen peptide preparations.

In a further preferred embodiment of the present invention, the collagen peptide obtained in method step c) is hydroxylated after performing method step d) in a method step x2) and a postlysal, i.e. after hydrolysis, ex vivo hydroxylated collagen peptide preparation is obtained in method step e).

Accordingly, the present invention further comprises a method for producing a collagen peptide preparation containing recombinant collagen peptides, in particular a post-lysally ex vivo hydroxylated collagen peptide preparation, comprising the method steps a) providing an expression system including at least one expression cassette, wherein the expression cassette includes at least one nucleotide sequence that encodes a collagen peptide having a molecular weight in a range of 8 to 100 kDa and wherein the expression system is not capable of hydroxylating proline residues, lysine residues or proline and lysine residues of the expressed collagen peptide, b) incubating the expression system under conditions that allow expression of the collagen peptide, c) obtaining the collagen peptide, d) hydrolyzing the collagen peptide under conditions that result in the production of a collagen peptide preparation, which includes collagen peptides having an average molecular weight of 1 to 7 kDa and a molecular weight in a range of 0.1 to 13.5 kDa and x2) ex vivo hydroxylation of the collagen peptides of the collagen peptide preparation obtained in step d), e) obtaining the collagen peptide preparation, in particular the post-lysally ex vivo hydroxylated collagen peptide preparation, hereinafter also referred to as collagen peptide preparation D.

In a preferred embodiment, the postlysally ex vivo hydroxylated collagen peptide preparation containing the recombinant collagen peptides produced according to the invention, i.e., collagen peptide preparation D, exhibits a biological activity in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes.

The post-lysally ex vivo hydroxylated collagen peptide preparation containing recombinant collagen peptides produced according to the invention, i.e., collagen peptide preparation D, preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, the same biological effectiveness as collagen peptide preparations isolated from natural sources, in particular non-recombinantly produced collagen peptide preparations.

The post-lysally ex vivo hydroxylated collagen peptide preparation containing recombinant collagen peptides produced according to the invention, i.e. collagen peptide preparation D, particularly preferably exhibits in at least one in vitro test for stimulating the synthesis of extracellular matrix proteins in osteoblasts, fibroblasts and chondrocytes, in particular in at least one, preferably in at least two, preferably in all of the in vitro tests shown in Examples 3 to 7, in particular Examples 3 to 5, for stimulating the synthesis of extracellular matrix proteins in osteoblasts, fibroblasts and chondrocytes, a better biological effectiveness than collagen peptide preparations isolated from natural sources, in particular non-recombinantly produced collagen peptide preparations.

According to one preferred embodiment of the present invention, the at least one nucleotide sequence of the at least one expression cassette is codon-optimized, i.e., those codons in the nucleotide sequence that are not used or are not preferably used, are replaced by those which are preferably used by the translation system of the provided expression system, in particular of the provided cell-based expression system, in particular of the host cell provided, without thereby changing the amino acid sequence of the encoded peptide or protein.

In one preferred embodiment of the present invention, the collagen peptide encoded by the nucleotide sequence is a collagen peptide from a vertebrate, in particular a mammal, for example a human or a non-human mammal, for example a horse, donkey, kangaroo, sheep, rodent, pig or cattle, a bird, for example a chicken, a fish, an amphibian, a reptile or an invertebrate, for example, a jellyfish.

The collagen peptide encoded by the nucleotide sequence preferably has an amino acid sequence in collagen of types I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, preferably type I, II or III, preferably type I, preferably type II, preferably type III.

The type I, II or III collagen peptide encoded by the nucleotide sequence is preferred, preferably type I or II, particularly preferably type I.

The collagen peptide encoded by the nucleotide sequence preferably includes an amino acid sequence occurring in collagen from vertebrates, in particular fish, amphibians, reptiles, birds and mammals, in particular in human, bovine, porcine, equine or avian collagen of types I, II or III, preferably type I, preferably type II, preferably type III.

The collagen peptide encoded by the nucleotide sequence particularly preferably includes an amino acid sequence occurring in human collagen, in particular in human type I collagen, preferably in the α1 chain of human type I collagen.

The collagen peptide encoded by the nucleotide sequence particularly preferably includes an amino acid sequence occurring in non-human collagen, in particular in non-human type I collagen, preferably in the α1 chain of non-human type I collagen, in particular an amino acid sequence occurring in bovine, porcine, equine or avian collagen.

The collagen peptide encoded by the nucleotide sequence is preferably a naturally occurring collagen peptide. In a further preferred embodiment of the present invention, the collagen peptide encoded by the nucleotide sequence is not a naturally occurring collagen peptide. The collagen peptide encoded by the nucleotide sequence is preferably a genetically modified collagen peptide. In a particularly preferred embodiment of the present invention, the collagen peptide encoded by the nucleotide sequence is a genetically modified collagen peptide, in which at least one amino acid of the amino acid sequence of a naturally occurring collagen peptide, preferably at least one non-essential amino acid, in particular Ala, Asn, Asp, Glu, Ser of the amino acid sequence of a naturally occurring collagen peptide, has been replaced by at least one very specific amino acid, in particular by at least one essential amino acid, in particular Ile, Leu, Lys, Met, Phe, Thr, Trp, Val, His, Cys, Tyr, particularly preferably Trp.

According to the invention, the collagen peptide encoded by the nucleotide sequence is a genetically modified collagen peptide, in which at least one amino acid, preferably at least one essential amino acid, in particular Ile, Leu, Lys, Met, Phe, Thr, Trp, Val, His, Cys, Tyr, particularly preferably Trp, has been added to the amino acid sequence of a naturally occurring collagen peptide. In this case, it may be provided according to the invention that the at least one amino acid, preferably the at least one essential amino acid, in particular Ile, Leu, Lys, Met, Phe, Thr, Trp, Val, His, Cys, Tyr, particularly preferably Trp, has been added N-terminally, C-terminally and/or within the amino acid sequence of a naturally occurring collagen peptide.

According to one preferred embodiment of the present invention, the at least one nucleotide sequence encodes a collagen peptide having a molecular weight in a range of preferably 8 to 95 kDa, preferably 8 to 90 kDa, preferably 8 to 85 kDa, preferably 8 to 80 kDa, preferably 9 to 95 kDa, preferably 9 to 90 kDa, preferably 9 to 85 kDa, preferably 9 to 80 kDa, preferably 10 to 95 kDa, preferably 10 to 90 kDa, preferably 10 to 85 kDa, preferably 10 to 80 kDa.

In a particularly preferred embodiment of the present invention, the hydrolysis is an enzymatic or acid-catalyzed hydrolysis, preferably an enzymatic hydrolysis, preferably an acid-catalyzed hydrolysis. The hydrolysis of the collagen peptide obtained in step c) is particularly preferably carried out by adding at least one bacterial or microbial protease, in particular at least one bacterial and/or microbial serine, cysteine, aspartate and/or metalloprotease, preferably at least one bacterial and/or microbial endoprotease, preferably of at least one bacterial and/or microbial exoprotease.

In a further preferred embodiment of the present invention, the collagen peptide is hydrolyzed in step d) under conditions which result in the production of a collagen peptide preparation containing collagen peptides having an average molecular weight of 1 to 3 kDa and a molecular weight in a range from 0.1 to 10 kDa, preferably 0.18 to 10 kDa, preferably 0.2 to 10 kDa.

In one preferred embodiment of the present invention, the collagen peptide is hydrolyzed in step d) under conditions which result in the production of a collagen peptide preparation containing collagen peptides having an average molecular weight of 1 to 5 kDa and a molecular weight in a range from 0.1 to 12 kDa, preferably 0.18 to 12 kDa, preferably 0.2 to 12 kDa.

The present invention also relates to a collagen peptide preparation produced using one of the aforementioned methods according to the invention, in particular a collagen peptide preparation containing collagen peptides having an average molecular weight of 1 to 7 kDa and a molecular weight in a range from 0.1 to 13.5 kDa, preferably 0.18 to 13.5, preferably 0.2 to 13.5.

In one preferred embodiment of the present invention, the collagen peptide preparation produced with one of the aforementioned methods according to the invention, in particular the collagen peptide preparation including collagen peptides having an average molecular weight of 1 to 7 kDa and having a molecular weight in a range from 0.1 to 13.5 kDa, is a non-hydroxylated, partially hydroxylated or fully hydroxylated collagen peptide preparation, preferably a non-hydroxylated collagen peptide preparation, preferably a partially hydroxylated collagen peptide preparation, preferably a fully hydroxylated collagen peptide preparation.

The collagen peptide preparation produced with one of the aforementioned methods according to the invention, in particular the collagen peptide preparation which has collagen peptides with an average molecular weight of 1 to 7 kDa and a molecular weight in a range from 0.1 to 13.5 kDa, is preferably a collagen peptide preparation, wherein at least 1%, preferably at least 2%, preferably at least 3%, preferably at least 4%, preferably at least 5%, preferably at least 10%, preferably at least 15%, preferably at least 20%, preferably at least 25%, preferably at least 30%, preferably at least 35%, preferably at least 40%, preferably at least 45%, preferably at least 50% of the prolyl residues, preferably the lysyl residues, particularly preferably the prolyl and lysyl residues, of the collagen peptides are hydroxylated, preferably hydroxylated in vivo, preferably hydroxylated ex vivo, in particular, are hydroxylated prel-ysally ex vivo or hydroxylated post-lysally ex vivo.

The collagen peptide preparation produced using one of the aforementioned methods according to the invention, in particular, the collagen peptide preparation which includes collagen peptides having an average molecular weight of 1 to 7 kDa and a molecular weight in a range from 0.1 to 13.5 kDa, is particularly preferably a collagen peptide preparation, wherein at most 95%, preferably at most 90%, preferably at most 85%, preferably at most 80%, preferably at most 75%, preferably at most 70%, preferably at most 65%, preferably at most 60%, preferably at most 55%, preferably at most 50%, preferably at most 45%, preferably at most 40%, preferably at most 35%, preferably at most 30%, preferably at most 25%, preferably at most 20%, preferably at most 15%, preferably at most 10%, preferably at most 5% of the prolyl residues, preferably the lysyl residues, particularly preferably the prolyl and lysyl residues of the collagen peptides are hydroxylated, preferably are hydroxylated in vivo, preferably are hydroxylated ex vivo, in particular are hydroxylated pre-lysally ex vivo or are hydroxylated post-lysally ex vivo.

In a further preferred embodiment of the present invention, the collagen peptide preparation produced with one of the aforementioned methods according to the invention, in particular the collagen peptide preparation that includes collagen peptides having an average molecular weight of 1 to 7 kDa and a molecular weight in a range from 0.1 to 13.5 kDa, is a collagen peptide preparation, wherein 0.5 to 80%, preferably 1 to 75%, preferably 5 to 70%, preferably 5 to 65%, preferably 10 to 60%, preferably 15 to 55%, preferably 20 to 50%, preferably 25 up to 50%, preferably 30 to 50%, preferably 35 to 50%, preferably 40 to 50% of the prolyl residues, preferably the lysyl residues, particularly preferably the prolyl and lysyl residues, of the collagen peptides are hydroxylated, preferably are hydroxylated in vivo, preferably are hydroxylated ex vivo, in particular are hydroxylated pre-lysally ex vivo or are hydroxylated post-lysally ex vivo.

In one preferred embodiment of the present invention, the collagen peptide preparation produced with one of the methods according to the invention, in particular the collagen peptide preparation that includes collagen peptides having an average molecular weight of 1 to 7 kDa and a molecular weight in a range from 0.1 to 13.5 kDa, is a collagen peptide preparation, whose collagen peptides are glycosylated. The collagen peptides are preferably glycosylated in vivo, preferably glycosylated ex vivo. At least 1%, preferably at least 2%, preferably at least 3%, preferably at least 4%, preferably at least 5%, preferably at least 6%, preferably at least 7%, preferably at least 8%, preferably at least 9%, preferably at least 10%, preferably at least 15%, preferably at least 20% of the hydroxyl residues are preferably glycosylated, preferably glycosylated in vivo, preferably glycosylated ex vivo.

In a further preferred embodiment of the present invention, the collagen peptide preparation produced using one of the methods according to the invention is a collagen peptide preparation whose collagen peptides are not glycosylated.

In one preferred embodiment of the present invention, the collagen peptide preparation, in particular the collagen peptide preparation that includes collagen peptides having an average molecular weight of 1 to 7 kDa and a molecular weight in a range from 0.1 to 13.5 kDa, is an in vivo hydroxylated collagen peptide preparation. i.e., collagen peptide preparation A.

In one preferred embodiment of the present invention, the collagen peptide preparation, in particular the collagen peptide preparation which includes collagen peptides having an average molecular weight of 1 to 7 kDa and a molecular weight in a range from 0.1 to 13.5 kDa, is a non-hydroxylated collagen peptide preparation, i.e., collagen peptide preparation B.

In a further preferred embodiment of the present invention, the collagen peptide preparation, in particular the collagen peptide preparation which includes collagen peptides having an average molecular weight of 1 to 7 kDa and a molecular weight in a range from 0.1 to 13.5 kDa, is an ex vivo hydroxylated collagen peptide preparation, i.e., collagen peptide preparation C or D.

The collagen peptide preparation, in particular the collagen peptide preparation that includes collagen peptides having an average molecular weight of 1 to 7 kDa and a molecular weight in a range from 0.1 to 13.5 kDa, is preferably a pre-lysal, i.e., before hydrolysis, collagen peptide preparation hydroxylated ex vivo, i.e., collagen peptide preparation C.

According to a further embodiment of the present invention, the collagen peptide preparation, in particular the collagen peptide preparation that includes collagen peptides having an average molecular weight of 1 to 7 kDa and a molecular weight in a range from 0.1 to 13.5 kDa, is a post-lysal, i.e., after hydrolysis, ex vivo hydroxylated collagen peptide preparation, i.e., collagen peptide preparation D.

The present invention also relates, in particular, to a collagen peptide preparation, in particular a hydroxylated or non-hydroxylated collagen preparation, which is produced by hydrolysis of collagen peptide produced recombinantly in a host cell having a molecular weight in the range from 8 to 100 kDa, the collagen peptide preparation including collagen peptides having an average molecular weight from 1 to 7 kDa and a molecular weight in a range from 0.1 to 13.5 kDa.

The presence of the characteristic peptides of the collagen peptide preparation that contribute to its effectiveness may be determined, in particular, by means of mass spectroscopy, preferably by means of ESI (electron spray ionization) or MALDI mass spectroscopy, the characteristic peptides appearing as peaks in the mass spectrum.

In a molecular weight distribution determined by means of MALDI mass spectroscopy, the characteristic peptides exhibit at least twice the intensity, more preferably at least four times the intensity, compared to their surroundings.

The collagen peptide preparations according to the invention, in particular the collagen peptide preparation A, the collagen peptide preparation B, the collagen peptide preparation C and the collagen peptide preparation D, may also include characteristic peptides having a size of 1,500 to 3,500 Da.

In a further preferred embodiment of the invention, the collagen peptide preparations according to the invention, in particular the collagen peptide preparation A, the collagen peptide preparation B, the collagen peptide preparation C and the collagen peptide preparation D, include a maximum of 5.5%, preferably a maximum of 5%, preferably a maximum of 4.5%, preferably a maximum of 4%, preferably at most 3.5%, collagen peptides having a size of <500 Da.

According to this embodiment, the particularly low percentage of peptides having a size of less than 500 Da advantageously improves the taste of the collagen peptide preparations compared to the preparations known in the prior art, in particular a reduced bitterness of the collagen peptide preparations.

Preferably 35 to 60%, preferably 35 to 55%, preferably 35 to 50%, preferably 36 to 48%, preferably 36 to 46%, preferably 37 to 45%, preferably 38 to 44% of the collagen peptides of the collagen peptide preparations according to the invention, in particular of the collagen peptide preparation A, of the collagen peptide preparation B, of the collagen peptide preparation C and of the collagen peptide preparation D have a size in the range of 1500 Da to 3500 Da.

The collagen peptide preparations according to the invention, in particular the collagen peptide preparation A, the collagen peptide preparation B, the collagen peptide preparation C and the collagen peptide preparation D, preferably include a maximum of 2.8%, preferably a maximum of 2.75%, preferably a maximum of 2.7%, preferably a maximum of 2.65%, preferably at most 2.6%, preferably at most 2.55%, preferably at most 2.5%, preferably at most 2.45%, preferably at most 2.4%, preferably at most 2.35%, preferably at most 2.3% collagen peptides having a size in the range from 7500 Da to 13500 Da.

According to one particularly preferred embodiment of the present invention, at least 93%, preferably at least 93.5%, preferably at least 94%, preferably at least 94.5%, preferably at least 95% of the collagen peptides of the collagen peptide preparations according to the invention, in particular of the collagen peptide preparation A, of the collagen peptide preparation B, of the collagen peptide preparation C and of the collagen peptide preparation D, have a size in the range from 500 Da to 7500 Da.

Preferably at least 94.5%, preferably at least 95%, preferably at least 95.5%, preferably at least 95.6%, preferably at least 95.7%, preferably at least 95.6%, preferably at least 95.7%, preferably at least 95.8%, preferably at least 95.9%, preferably at least 96%, preferably at least 96.1%, preferably at least 96.2%, preferably at least 96.3%, preferably at least 96.4%, preferably at least 96.5% of the collagen peptides of the collagen peptide preparations according to the invention, in particular of the collagen peptide preparation A, of the collagen peptide preparation B, of the collagen peptide preparation C and of the collagen peptide preparation D, have a size in the range from 500 Da to 13500 Da.

In a preferred embodiment, according to the present invention, the collagen peptide preparation is administered locally, in particular topically, or systemically, in particular enterally, preferably orally.

According to one preferred embodiment of the invention, the collagen peptide preparation is administered in the form of a food supplement. The food supplement according to the invention is particularly advantageously in the form of a solution, suspension or gel, for example, in an ampoule, as granules or powder. Due to its good solubility, the collagen peptide preparation may also be added to various beverages without causing cloudiness.

According to one preferred embodiment of the present invention, the food supplement provided according to the invention contains, in addition to the collagen peptide preparation, no further proteins or protein hydrolyzates.

According to one embodiment of the invention, the food supplement according to the invention contains, in addition to the collagen peptide preparation, no further physiologically active constituents, in particular no proteins or protein hydrolysates.

The invention also relates to a product comprising a collagen peptide preparation according to the invention and at least one additive.

The subject matter of the invention is also a food supplement comprising a collagen preparation according to the invention and at least one further component, in particular at least one food-acceptable additive.

In one embodiment, the collagen peptide preparation may be added to a food or luxury food product, for example, a chocolate bar, protein bar, cereal bar, milk, milk products, for example yogurt, whey or quark and milk substitute, for example, soy milk, rice milk, almond milk and coconut milk (so-called functional food).

The subject matter of the invention is thus also a food or luxury food item comprising a collagen preparation according to the invention.

According to the invention, it may further be provided that the collagen peptide preparation is administered in the form of a pharmaceutical composition. The pharmaceutical composition according to the invention is administered particularly advantageously, for example, in the form of tablets, lozenges, chewable tablets, capsules, bite capsules, coated tablets, lozenges, juices, gels or ointments.

The present invention also relates to a pharmaceutical composition comprising a collagen peptide preparation according to the invention and at least one pharmaceutically acceptable additive.

In a further embodiment, it may be provided that the collagen peptide preparation is administered in the form of a cosmetic composition. The cosmetic composition according to the invention is particularly advantageously administered, for example, in the form of lotions, ointments, creams, gels, powders, syringes or sprays.

The present invention also relates to a cosmetic composition comprising a collagen peptide preparation according to the invention and at least one skin-compatible additive.

If the collagen peptide preparation according to one preferred embodiment of the invention is not used as the sole physiologically active component of a product, in particular of a food supplement, of a food or luxury food item, of a pharmaceutical composition or of a cosmetic composition, it may be combined with one or more other components that have a positive effect on general health, in particular on endurance performance. Such components are preferably selected from the group consisting of vitamin C, vitamins of the B, D, E and K series, omega-3 fatty acids, omega-6 fatty acids, conjugated linolenic acids, caffeine and its derivatives, guarana extract, green tea extract, epigallocatechin gallate, creatine, L-carnitine, α-lipoic acid, N-acetylcysteine, NADH, D-ribose, magnesium aspartate, antioxidants such as anthocyanins, carotenoids, flavonoids, resveratrol, glutathione and superoxide dismutase (SOD), cannabidinoids such as cannabidiol (CBD), adaptogens such as *Rhodiola rosea, Panax ginseng, Withania somnifera*, shiitake, *Ganoderma lucidum Lepidium meyenii*, minerals such as iron, magnesium, calcium, zinc, selenium and phosphorus, as well as other proteins, hydrolysates and peptides such as soy, wheat and whey protein.

In one preferred embodiment of the invention, the collagen peptide preparation is administered in an amount of 1 to 40 g per day, preferably from 1 to 30 g per day, preferably from 1 to 20 g per day, preferably from 1 to 15 g per day, preferably from 2.5 to 30 g per day, preferably 2.5 to 20 g per day, preferably 2.5 to 15 g per day, preferably 2.5 to 10 g per day, preferably 4 to 15 g per day, preferably 4 to 12 g per day, more preferably from 5 to 25 g per day, preferably from 5 to 15 g per day, more preferably from 10 to 25 g per day, preferably from 12 to 22 g per day, and in particular from 12.5 to 20 g per day, particularly preferably 6 to 15 g per day, in particular from 2.5 to 7.5 g per day, preferably 2.5 to 5 g per day.

The present invention also relates to a collagen peptide preparation according to the invention to be applied in a therapeutic method for maintaining and improving bone health, for preventing and/or treating osteoporosis, for preventing and/or treating sarcopenia, for preventing and/or treating degenerative loss of muscle mass, for improving muscle strength, for stimulating fat loss, and for reducing body weight.

In a preferred embodiment, the present invention also relates to the collagen peptide preparation according to the invention to be applied in a method for preventing and/or treating bone diseases, in particular osteoporosis.

In one preferred embodiment, the present invention relates to the collagen peptide preparation according to the invention to be applied in a method for preventing and/or treating sarcopenia.

In a preferred embodiment, the present invention relates to the collagen peptide preparation according to the invention to be applied in a method for preventing and/or treating degenerative loss of muscle mass.

In a preferred embodiment, the present invention relates to the collagen peptide preparation according to the invention to be applied in a method for preventing and/or treating cartilage diseases, in particular arthrosis or arthritis.

In a preferred embodiment, the present invention relates to the collagen peptide preparation according to the invention to be applied in a method for improving muscle strength.

In a preferred embodiment, the present invention relates to the collagen peptide preparation according to the invention to be applied in a method for preventing and/or treating a pathological condition characterized by reduced mitochondrial activity, in particular for preventing and/or treating a pathological condition characterized by reduced endurance.

In a preferred embodiment, the present invention relates to the collagen peptide preparation according to the invention to be applied in a method for stimulating fat breakdown.

In a preferred embodiment, the present invention relates to the collagen peptide preparation according to the invention to be applied in a method for reducing body weight.

In a preferred embodiment, the present invention relates to the collagen peptide preparation according to the invention to be applied in a method for preventing and/or treating degenerative joint diseases, in particular osteoarthritis, rheumatoid arthritis, rheumatic diseases, spondylitis and/or fibromyalgia.

In a preferred embodiment, the present invention relates to the collagen peptide preparation according to the invention to be applied in a method for preventing and/or treating diseases of the tendons or ligaments.

In a preferred embodiment, the present invention relates to the collagen peptide preparation according to the invention to be applied in a method for preventing and/or treating skin diseases, in particular psoriasis vulgaris, acne, atopic dermatitis, chronic pruritus and/or rosacea.

In a preferred embodiment, the present invention relates to the collagen peptide preparation according to the invention to be applied in a method for treating wounds, in particular chronic wounds, acute wounds and/or burns.

In a preferred embodiment, the present invention relates to the collagen peptide preparation according to the invention to be applied in a method for preventing and/or treating degenerative nerve diseases.

In a preferred embodiment, the present invention relates to the collagen peptide preparation according to the invention to be applied in a method for preventing and/or treating dementia.

In a preferred embodiment, the present invention relates to the collagen peptide preparation according to the invention to be applied in a method for preventing and/or treating Alzheimer's disease.

In a preferred embodiment, the present invention relates to the collagen peptide preparation according to the invention to be applied in a method for preventing and/or treating a pathological condition characterized by a reduction in mental performance.

In a preferred embodiment, the present invention relates to the collagen peptide preparation according to the invention to be applied in a method for preventing and/or treating diseases associated with malfunctions of the blood-brain barrier, in particular the structure and/or function of the meninges.

In a preferred embodiment, the present invention relates to the collagen peptide preparation according to the invention to be applied in a method for preventing and/or treating bowel diseases, in particular chronic inflammatory bowel diseases.

In a preferred embodiment, the present invention relates to the collagen peptide preparation according to the invention for use in a method for the prevention and/or treatment of diseases of the cardiovascular system, in particular the structure and/or function of the blood vessels, in particular the vascular wall, in particular for prevention and/or treatment of high blood pressure and/or circulatory disorders.

In a preferred embodiment, the present invention relates to the collagen peptide preparation according to the invention to be applied in a method for preventing and/or treating diseases of the tooth holding apparatus.

The present invention also relates to a collagen peptide preparation according to the invention to be applied in a non-therapeutic method for maintaining and improving bone health, for preventing osteoporosis, for preventing and/or treating sarcopenia, for preventing degenerative loss of muscle mass, for improving muscle strength, for stimulating fat loss, for reducing body weight and/or for preventing degenerative joint diseases.

In one preferred embodiment, the present invention also relates to the non-therapeutic use of the collagen peptide preparation according to the invention for the visual and structural improvement of the skin, in particular for reducing wrinkles, improving skin elasticity, increasing the skin tone, increasing the moisture content of the skin, reducing cellulite and/or reducing stretch marks, especially stretch marks.

In a further preferred embodiment, the present invention relates to the non-therapeutic use of the collagen peptide preparation according to the invention for accelerating the growth of nails and/or reducing the fragility of nails.

In a preferred embodiment, the present invention also relates to the non-therapeutic use of the collagen peptide preparation according to the invention for the optical and structural improvement of the hair, in particular for improving the hair quality, reducing split ends and/or reducing/delaying hair loss.

In a further preferred embodiment, the present invention relates to the non-therapeutic use of the collagen peptide preparation according to the invention for increasing the number of mitochondria and/or mitochondrial activity.

In a further preferred embodiment, the present invention relates to the non-therapeutic use of the collagen peptide preparation according to the invention for improving endurance performance.

In a further preferred embodiment, the present invention relates to the non-therapeutic use of the collagen peptide preparation according to the invention for improving mental performance.

In a preferred embodiment of the present invention, the collagen peptide preparation according to the invention is used alone, i.e., without further substances, for use in one of the applications provided according to the invention.

In a further embodiment of the present invention, the collagen peptide preparation according to the invention is used as the sole agent exhibiting biological activity in an application provided according to the invention.

In a further preferred embodiment, the collagen peptide preparation according to the invention is used together with at least one further agent, in particular a further biologically active agent, in an application provided according to the invention.

The present invention also relates to methods for preventing and/or treating the aforementioned indications, in particular of the aforementioned therapeutic indications, according to which the human or animal body is administered a sufficient amount of the collagen peptide preparation according to the invention for the therapeutic purpose, optionally with an additive.

The present invention also relates to a non-therapeutic method for improving muscle strength, for increasing muscle mass, for stimulating fat loss, for reducing body weight, for maintaining and/or improving bone health, for maintaining and/or improving skin health, for maintaining and/or improving the intestinal health, for maintaining and/or improving the blood vessel structure, for maintaining and/or improving the health of the cardiovascular system, for maintaining and/or improving the gums, for maintaining and/or improving the health of the nails and hair of a human or animal body, for maintaining and/or increasing the number of mitochondria and/or mitochondrial activity, for maintaining and/or improving endurance performance or for maintaining and/or improving mental performance, whereby the human or animal body is administered at least one collagen peptide preparation according to the invention.

The present invention also relates to a collagen peptide preparation according to the invention to be applied in a method for producing films, foils and coatings. The coatings may be, for example, paints and varnishes, in particular paints and varnishes with special optical effects, or coatings for producing self-cleaning surfaces.

In a preferred embodiment, the term "collagen" in connection with the present invention is understood in a manner customary in the art, in particular as defined, for example, in WO 01/34646. In a preferred embodiment, the term "collagen" relates to collagen types I to XXVII. In a further preferred embodiment, the term "collagen" is understood to mean a peptide that includes the sequence glycine-proline, glycine-4-hydroxyproline or glycine-X-4-hydroxyproline, preferably the repetitive motif $(Gly-X-Y)_n$, where X and Y may be any amino acid, preferably proline and 4-hydroxyproline. The term "collagen" is particularly preferably understood to mean a peptide having the repetitive motif $(Gly-Pro-Y)_n$ and/or $(Gly-X-Hyp)_m$, where X and Y may be any amino acid.

In connection with the present invention, the term "gelatin" is preferably understood in a manner customary in the art, in particular as defined, for example, in WO 01/34646.

In connection with the present invention, the term "collagen peptide" is preferably understood to mean a peptide which has an amino acid sequence occurring in collagen as defined above. A "collagen peptide" is preferably also understood to mean a genetically modified collagen peptide, which was obtained by modifying the amino acid sequence of a naturally occurring collagen peptide, wherein the collagen peptide preparation obtained from the "collagen peptide" obtained in step e) of the method according to the invention exhibits preferably in at least one in vitro test for stimulating the synthesis of extracellular matrix proteins in osteoblasts, fibroblasts and chondrocytes, in particular in at least one, preferably in at least two, preferably in all of the in vitro stimulation tests shown in Examples 3 to 7, in particular Examples 3 to 5, for stimulating extracellular matrix proteins in osteoblasts, fibroblasts and chondrocytes, a biological activity, preferably the same biological activity as collagen peptide preparations isolated from natural sources, in particular non-recombinantly produced collagen peptide preparations, particularly preferably a better biological effectiveness than collagen peptide preparations isolated from natural sources, in particular non-recombinantly produced collagen peptide preparations.

In connection with the present invention, the term "recombinant DNA" denotes an artificially produced or manipulated DNA molecule, which has been produced in vitro by means of genetic engineering methods. In a preferred embodiment, the recombinant DNA is composed of components from different organisms of origin.

In connection with the present invention, a "recombinant or recombinantly produced collagen peptide" is understood to mean a collagen peptide encoded by recombinant DNA.

In connection with the present invention, the term "expression cassette" is understood to mean a DNA segment, which is responsible for the transcription of the information encoded in this segment into an RNA, in particular into an mRNA, and includes at least one promoter and one protein-encoding nucleotide sequence, usually has at least one promoter, at least one protein-encoding nucleotide sequence and optionally a terminator.

In connection with the present invention, a "nucleotide sequence" is understood to mean the sequence of the nucleotides of a nucleic acid, in particular a nucleic acid strand, in particular a DNA or RNA strand. A "nucleotide sequence" is therefore to be understood both as an informational unit and as the DNA or RNA strand physically manifesting this information.

In connection with the present invention, an "expression system" is understood to mean a system in which a targeted and controlled protein biosynthesis may take place. According to the invention, the term "expression system" encompasses both cell-free expression systems in which the components necessary for protein biosynthesis are not present within a cell, i.e., protein synthesis takes place outside of a cell, as well as cell-based expression systems in which protein biosynthesis takes place within a living cell. In connection with the present invention, a cell-free expression system is preferably a lysate or an extract from E. coli, insect cells, wheat germ, tobacco cells or mammalian cells, in particular CHO cells or reticulocytes from rabbits, which contains the components necessary for protein biosynthesis, in particular a translation and a transcription system.

In connection with the present invention, a "host cell" is understood to mean a living cell which is capable of expressing peptides or proteins encoded in foreign DNA, in particular in recombinant DNA.

In connection with the present invention, the terms "pre-lysal" and "post-lysal" denote a point in time before or after the hydrolysis, in particular before or after enzymatic or acid-catalyzed hydrolysis.

In connection with the present invention, the term "incubating" is understood to mean both the cultivation of a cell-based expression system, in particular of a host cell, and the action of certain conditions on a cell-free expression system.

According to the invention, the terms "obtaining the collagen peptide" according to method step c) and "obtaining the collagen peptide preparation" according to method step e) are understood to mean a method known to the person skilled in the art for isolating the collagen peptide or the collagen peptide preparation from a composition containing multiple components by means of known isolation methods such as, for example, centrifugation methods, in particular differential centrifugation and/or density gradient centrifugation, chromatographic methods, in particular gel filtration, ion exchange, affinity and/or high-performance liquid chromatography, electrophoresis methods, filtration methods and/or extraction methods, wherein an enrichment and purification of the relevant component from the composition containing multiple components may be achieved, preferably via the sequential application of multiple isolation methods.

According to the invention, "conditions which enable the expression of the collagen peptide" are understood to mean conditions, such as, in particular, temperature, pressure, time, light and the presence or absence of inducers and/or repressors, which activate or intensify an expression of the collagen peptide. In one preferred embodiment, the expression of the collagen peptide takes place in the context of a high cell density fermentation, in particular under high pressure, preferably high pressure air. The specific conditions which enable an expression of the collagen peptide are known to the person skilled in the art and depend on the expression system used and the expression cassette used, in particular, on the promoter contained therein. The expression of the collagen peptide may be a constitutive or inducible expression, depending on the structure of the expression cassette.

In connection with the present invention, the term "hydrolyzing the collagen peptide under conditions which result in the production of a collagen peptide preparation" is understood to mean those conditions, in particular the type of hydrolysis, possibly the type and amount of the at least one enzyme used for the hydrolysis, pH value, hydrolysis time, and hydrolysis temperature, which result in the obtaining of collagen peptides having an average molecular weight of 1 to 7 kDa and a molecular weight in the range from 0.1 to 13.5 kDa from a recombinantly produced collagen peptide having a molecular weight in a range from 8 to 100 kDa. Suitable conditions are specified, for example, in Example 1, for obtaining collagen peptides having an average molecular weight of 1 to 7 kDa and having a molecular weight in the range from 0.1 to 13.5 kDa from a recombinantly produced collagen peptide having a molecular weight in a range from 8 to 100 kDa.

The percentages cited in connection with the molecular weight distribution of the collagen peptides in the collagen peptide preparations according to the invention relate to % by weight in relation to all collagen peptides contained in the relevant collagen peptide preparation.

In connection with the present invention, the terms "comprising" and "including" are understood to mean that in addition to the elements explicitly covered by these terms, further elements that are not explicitly mentioned may be added. In connection with the present invention, these terms are also understood to mean that only the explicitly mentioned elements are included and no further elements are present. In this particular embodiment, the meaning of the terms "comprising" and "including" is synonymous with the term "consisting of." In addition, the terms "comprising" and "including" also include compositions which, in addition to the explicitly named elements, also contain other elements not mentioned, but which are functionally and qualitatively subordinate. In this embodiment, the terms "comprising" and "including" are synonymous with the term "consisting essentially of."

In connection with the present invention, the term "and/or" is understood to mean that all members of a group which are connected by the term "and/or" are disclosed both as alternatives to one another and also cumulatively to one another in any combination. For the expression "A, B and/or C," this means that the following disclosure content is to be understood to mean: a) A or B or C or b) (A and B) or c) (A and C) or d) (B and C) or e) (A and B and C).

Further preferred embodiments result from the dependent claims.

The invention is described below without restricting the general inventive concept with reference to figures, tables and the associated exemplary embodiments.

FIG. 1 shows the percentages of individual collagen peptides of comparative products 1 and 2 and of the collagen peptide preparations according to Examples 1.3, 1.4 and 1.5 in defined molecular weight ranges.

Figure 5:
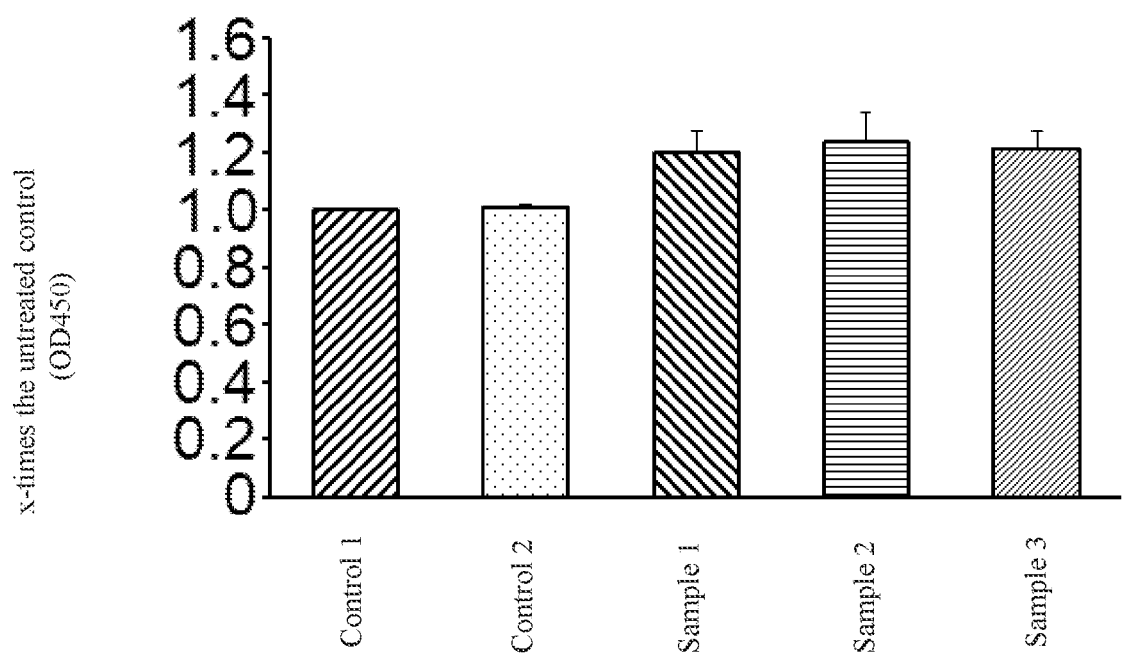

FIG. 5 shows a comparison of the stimulation of the collagen synthesis of primary human fibroblasts in the absence of a collagen peptide (control 1), in the presence of 0.5 mg/ml of a 100 kDa collagen peptide (control 2), of a non-hydroxylated collagen peptide preparation according to the invention having an average molecular weight of 1.8 kDa (sample 1), of a non-hydroxylated collagen peptide preparation according to the invention having an average molecular weight of 2.4 kDa (sample 2) or of a non-hydroxylated collagen peptide preparation according to the invention having an average molecular weight of 3.4 kDa (sample 3). The error bars show the standard deviation.

Figure 6:
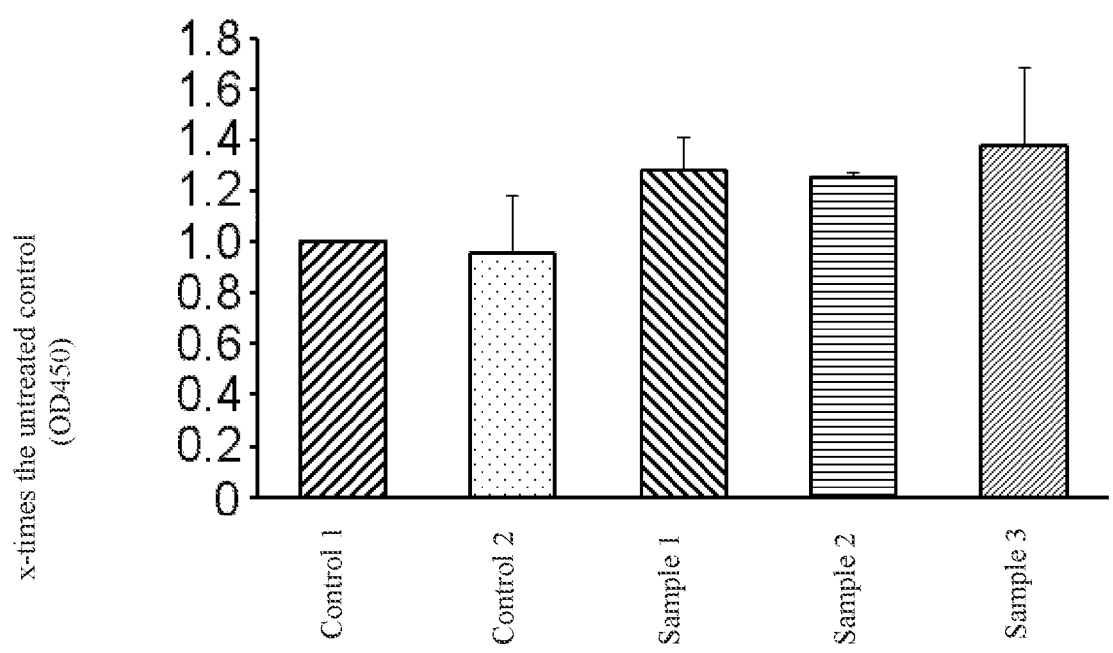

FIG. 6 shows a comparison of the stimulation of the elastin synthesis of primary human fibroblasts in the absence of a collagen peptide (control 1), in the presence of 0.5 mg/ml of a 100 kDa collagen peptide (control 2), of a non-hydroxylated collagen peptide preparation according to the invention having an average molecular weight of 1.8 kDa (sample 1), of a non-hydroxylated collagen peptide preparation according to the invention having an average molecular weight of 2.4 kDa (sample 2) or of a non-hydroxylated collagen peptide preparation according to the invention having an average molecular weight of 3.4 kDa (sample 3). The error bars show the standard deviation.

Figure 7:
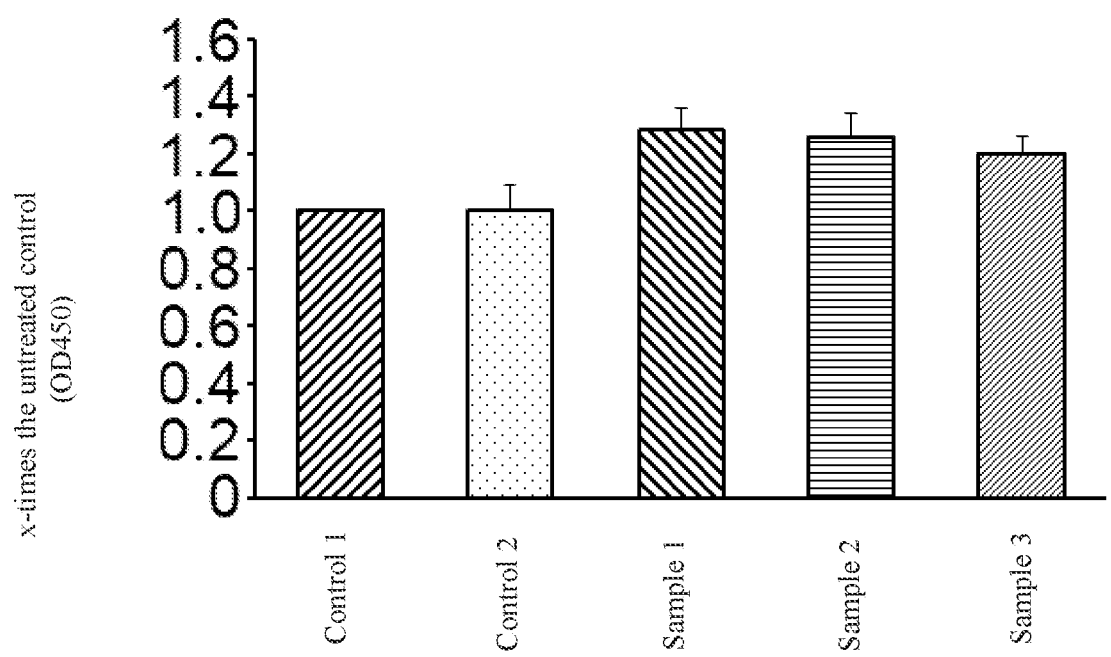

FIG. 7 shows a comparison of the stimulation of the proteoglycan synthesis of primary human fibroblasts in the absence of a collagen peptide (control 1), in the presence of 0.5 mg/ml of a 100 kDa collagen peptide (control 2), of a non-hydroxylated collagen peptide preparation according to the invention having an average molecular weight of 1.8 kDa (sample 1), of a non-hydroxylated collagen peptide preparation according to the invention having an average molecular weight of 2.4 kDa (sample 2) or of a non-hydroxylated collagen peptide preparation according to the invention having an average molecular weight of 3.4 kDa (sample 3). The error bars show the standard deviation.

Figure 8:
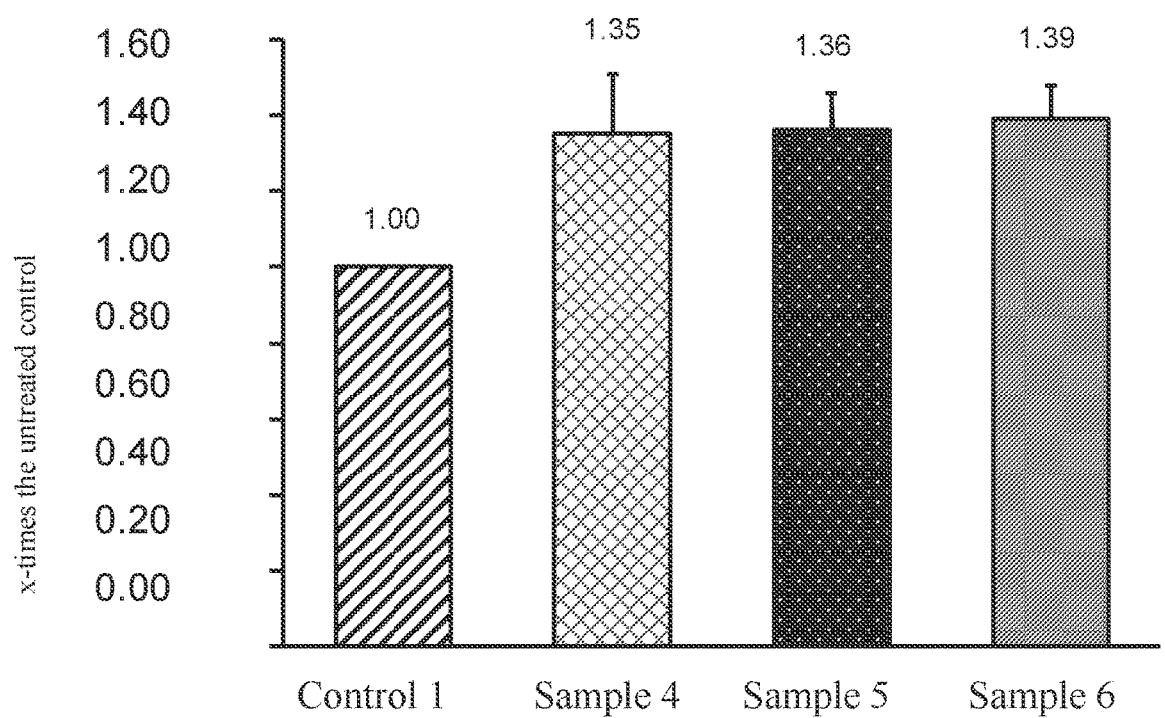

FIG. 8 shows a comparison of the stimulation of the collagen synthesis of primary human fibroblasts in the absence of a collagen peptide (control 1), in the presence of 0.5 mg/ml of a hydroxylated collagen peptide preparation according to the invention having an average molecular weight of 7 kDa (sample 4), of a hydroxylated collagen peptide preparation according to the invention having an average molecular weight of 5.6 kDa (sample 5) or of a hydroxylated collagen peptide preparation according to the invention having an average molecular weight of 1.3 kDa (sample 6). The error bars show the standard deviation.

Figure 9:
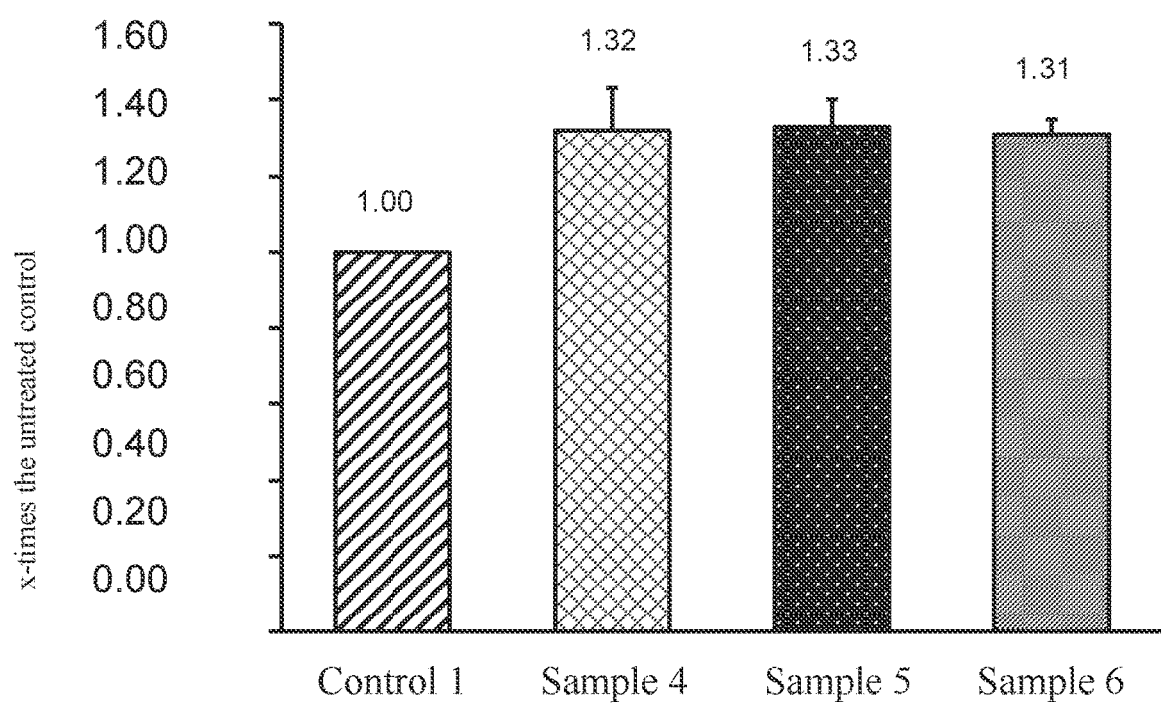

FIG. 9 shows a comparison of the stimulation of the elastin synthesis of primary human fibroblasts in the absence of a collagen peptide (control 1), in the presence of 0.5 mg/ml of a hydroxylated collagen peptide preparation according to the invention having an average molecular weight of 7 kDa (sample 4), of a hydroxylated collagen peptide preparation according to the invention having an average molecular weight of 5.6 kDa (sample 5) or of a hydroxylated collagen peptide preparation according to the invention having an average molecular weight of 1.3 kDa (sample 6). The error bars show the standard deviation.

Figure 10:
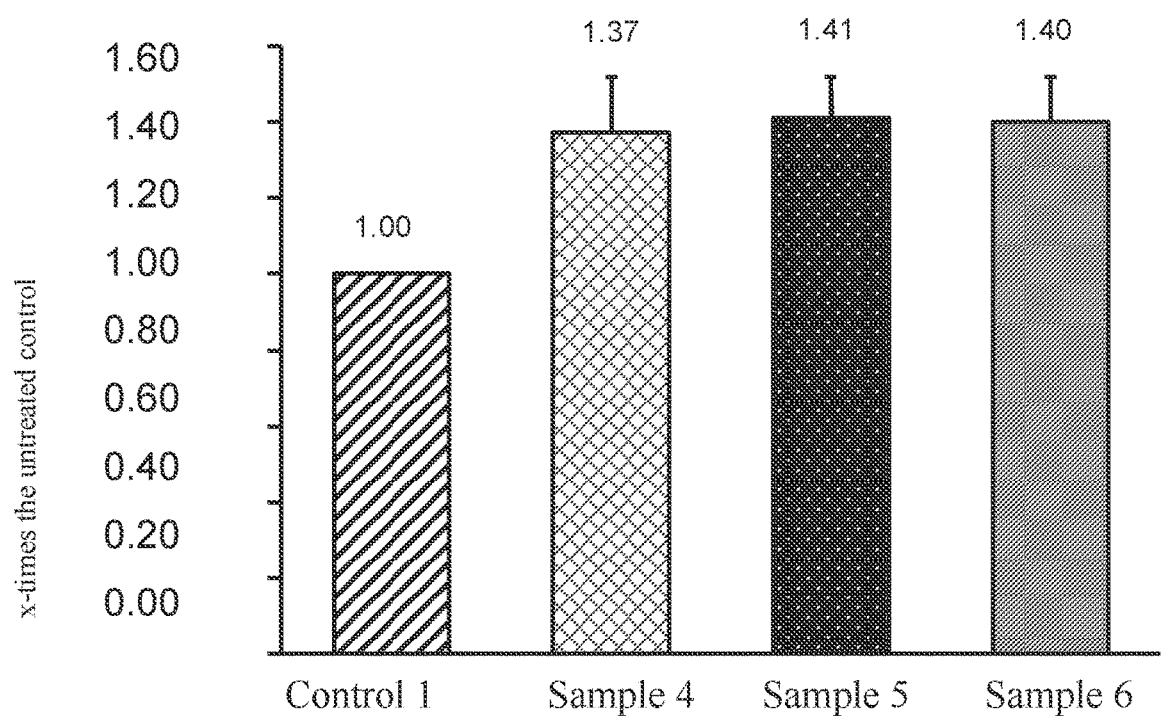

FIG. 10 shows a comparison of the stimulation of the proteoglycan synthesis of primary human fibroblasts in the absence of a collagen peptide (control 1), in the presence of 0.5 mg/ml of a hydroxylated collagen peptide preparation according to the invention having an average molecular weight of 7 kDa (sample 4), of a hydroxylated collagen peptide preparation according to the invention having an average molecular weight of 5.6 kDa (sample 5) or of a hydroxylated collagen peptide preparation according to the invention having an average molecular weight of 1.3 kDa (sample 6). The error bars show the standard deviation.

EXAMPLES

Example 1—Production of Collagen Peptides 1.1 Hydrolysis of a Non-Hydroxylated Collagen Peptide of Bovine Origin with a Size of 45 kDa, Produced Recombinantly in *Pichia pastoris*, with Neutral Protease A 0.789% collagen solution was initially heated to 50° C. in a 50 ml bottle in the cryostat. Then 200 ppm $CaCl_2 \times 2H_2O$ (based on the dry substance (TS) of the collagen) were added to the temperature-controlled collagen solution and the pH value of the solution was adjusted to 6.2 with a 10% NaOH solution. In a next step, 0.8% Sumizyme BNP-L (based on TS of the collagen) was added to the collagen solution.

The average molecular weight of the collagen peptides after a hydrolysis time of 180 minutes was determined to be 5.04 kDa.

1.2 Hydrolysis of a Non-Hydroxylated Collagen Peptide of Bovine Origin with a Size of 45 kDa, Produced Recombinantly in *Pichia pastoris*, with Alkaline Protease A 0.792% collagen solution was initially heated to 63° C. in a 50 ml bottle in the cryostat. Then 200 ppm $CaCl_2 \times 2H_2O$ (based on TS of the collagen) were added to the temperature-controlled collagen solution and the pH value of the solution was adjusted to 7.75 with 10% NaOH solution. In a next step, 0.3% Alcalase 2.4 L (based on TS of the collagen) was added to the collagen solution.

The average molecular weight of the collagen peptides after a hydrolysis time of 180 minutes was determined to be 3.01 kDa.

1.3 Hydrolysis of a Non-Hydroxylated Collagen Peptide of Human Origin with a Size of 25 kDa Produced Recombinantly in *Pichia pastoris* with Alkaline Protease A 2.85% collagen solution was initially heated to 63° C. in a 50 ml bottle in the cryostat. Then 200 ppm $CaCl_2 \times 2H_2O$ (based on TS of the collagen) were added to the tempered collagen solution and the pH value of the solution was adjusted to 7.6 with 10% NaOH solution. In a next step, 0.3% Alcalase 2.4 L (based on TS of the collagen) was added to the collagen solution.

The average molecular weight of the collagen peptides after a hydrolysis time of 45 minutes was 1.8 kDa.

1.4 Hydrolysis of a Non-Hydroxylated Collagen Peptide of Human Origin with a Size of 100 kDa Produced Recombinantly in *Pichia pastoris* with Alkaline Protease First, a 2.85% collagen solution in a 50 ml bottle was heated to 63° C. in the cryostat. Then 200 ppm $CaCl_2 \times 2H_2O$ (based on TS of the collagen) were added to the temperature-controlled collagen solution and the pH value of the solution was adjusted to 7.6 with 10% NaOH solution. Then 0.4% Alcalase 2.4 L (based on TS of the collagen) was added to the collagen solution.

After a hydrolysis time of 45 minutes, the solution included collagen peptides having an average molecular weight of 2.4 kDa. The resulting collagen peptide preparation according to the invention was used as sample 2 in Example 6.

1.5 Hydrolysis of a Non-Hydroxylated Collagen Peptide of Human Origin with a Size of 100 kDa Produced Recombinantly in *Pichia pastoris* with Alkaline Protease A 1.5% collagen solution was heated to 63° C. in a 50 ml bottle in the cryostat. Then 200 ppm $CaCl_2 \times 2H_2O$ (based on TS of the collagen) were added to the temperature-controlled collagen solution and the pH value of the solution was adjusted to 7.6 with 10% NaOH solution. Finally, 0.3% Alcalase 2.4 L (based on TS of the collagen) was added to the collagen solution.

The average molecular weight of the collagen peptides after a hydrolysis time of 60 minutes was 1.8 kDa. The resulting collagen peptide preparation according to the invention was used as sample 1 in Example 6.

1.6 Hydrolysis of a Non-Hydroxylated Collagen Peptide of Human Origin with a Size of 25 kDa Produced Recombinantly in *Pichia pastoris* with Alkaline Protease A 2.85% collagen solution was initially heated to 63° C. in a 50 ml bottle in the cryostat. Then 200 ppm $CaCl_2 \times 2H_2O$ (based on TS of the collagen) were added to the tempered collagen solution and the pH value of the solution was adjusted to 7.6 with 10% NaOH solution. In a next step, 0.1% Alcalase 2.4 L (based on TS of the collagen) was added to the collagen solution.

The average molecular weight of the collagen peptides after a hydrolysis time of 60 minutes was 3.4 kDa. The resulting collagen peptide preparation according to the invention was used as sample 3 in Example 6.

1.7 Hydrolysis of a Hydroxylated Collagen Peptide of Bovine Origin with a Size of 45 kDa Produced Recombinantly in *Pichia pastoris* with Alkaline Protease A 5.53% collagen solution was initially heated to 55° C. in a 250 ml glass bottle in the cryostat. Then 200 ppm $CaCl_2 \times 2H_2O$ (based on TS of the collagen) were added to the temperature-controlled collagen solution and the pH value of the solution was adjusted to 7.59 with 2% NaOH solution. In a next step, 0.2% Alcalase 2.4 L (based on TS of the collagen) was added to the collagen solution.

The average molecular weight of the collagen peptides after a hydrolysis time of 150 min was determined to be 7 kDa. The resulting collagen peptide preparation according to the invention was used as sample 4 in Example 7.

1.8 Hydrolysis of a Hydroxylated Collagen Peptide of Bovine Origin with a Size of 45 kDa Produced Recombinantly in *Pichia pastoris* with Alkaline Protease A 5.00% collagen solution was initially heated to 55° C. in a 100 ml glass bottle in the cryostat. Then 200 ppm $CaCl_2 \times 2H_2O$ (based on TS of the collagen) were added to the temperature-controlled collagen solution and the pH value of the solution was adjusted to 7.60 with 2% NaOH solution. Then 0.25% NZ37071 (based on TS of the collagen) was added to the collagen solution.

The average molecular weight of the collagen peptides after a hydrolysis time of 240 minutes was 5.6 kDa. The resulting collagen peptide preparation according to the invention was used in Example 7 as sample 5.

1.9 Hydrolysis of a Hydroxylated Collagen Peptide of Bovine Origin with a Size of 45 kDa Produced Recombinantly in *Pichia pastoris* with Alkaline Protease Starting from the collagen peptide hydrolyzate obtained according to Example 1.7, the higher molecular weight components of the hydrolyzate were removed by means of a concentrator (e.g. Vivaspin 20) with a size exclusion membrane of 5000 Da.

An average molecular weight of 1.3 kDa was ascertained for the collagen peptides thus obtained. The collagen peptide preparation according to the invention was used as sample 6 in example 7.

1.10 Gel Chromatographic Analysis of the Collagen Peptide Hydrolysates

The molecular weight distribution of the collagen peptide hydrolyzates obtained in Examples 1.3 to 1.5 and of two commercially available comparison products having an average molecular weight of 2.3 kDa and 1.7 kDa were determined by means of gel chromatography (Knauer, Germany). The statistical analysis was carried out using the WinGPC software (company PSS GmbH, Mainz, Germany). The following parameters were used for gel chromatography:

| | |
|---|---|
| Stationary phase: | TSK 2000 SW XL (TOSOH Bioscience GmbH) |
| Mobile phase: | 0.4 mol/l sodium dihydrogen phosphate, pH 5.3 |
| Flow rate: | 0.5 ml/min |
| Calibration standard: | defined collagen type 1 fragments (FILK) |
| Detection: | UV detection at 214 nm (Knauer) |
| Sample concentration: | 1% |

Figure 1:
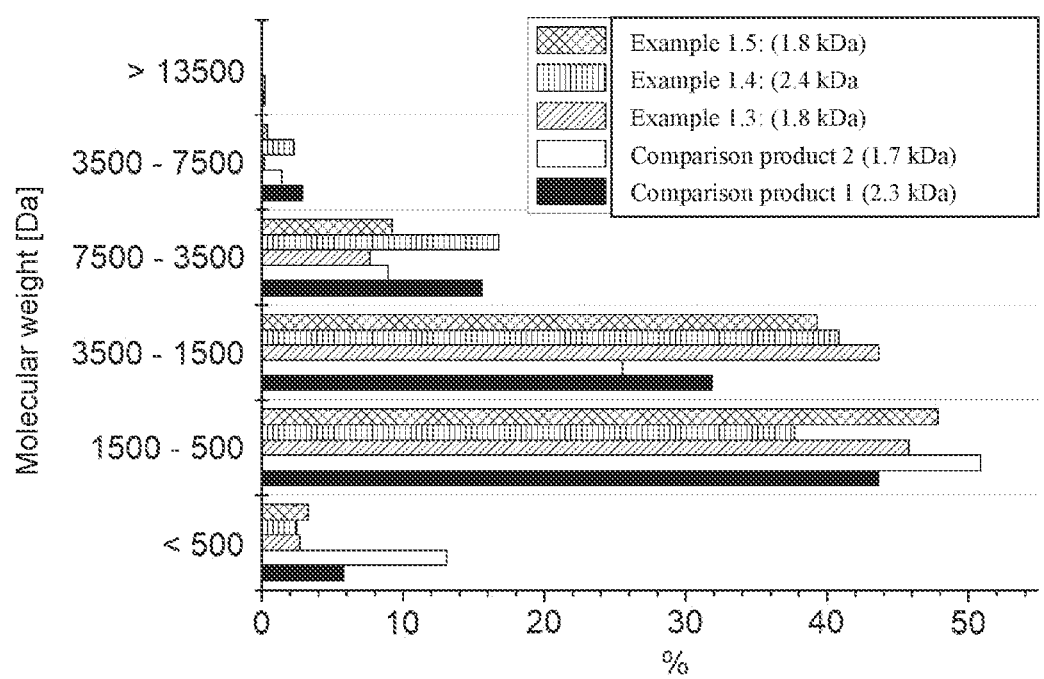

For the different collagen peptide hydrolyzates, the percentages of individual collagen peptides shown in Table 1 and in FIG. 1 were obtained in defined molecular weight ranges.

TABLE 1

Evaluation of the percentages of the individual collagen peptides in defined molecular weight ranges. The analysis was carried out by means of gel chromatography using defined type 1 collagen peptide standards.

| Molecular weight range of the individual peptides in Da | Comparison product 1 2.3 kDa Percentage wt.-% | Comparison product 2 1.7 kDa Percentage wt-% | Example 1.3 Percentage wt.-% | Example 1.4 Percentage wt-% | Example 1.5 Percentage wt.-% |
|---|---|---|---|---|---|
| <500 | 5.81 | 13.09 | 2.72 | 2.47 | 3.26 |
| 1500-500 | 43.63 | 50.84 | 45.78 | 37.69 | 47.84 |
| 3500-1500 | 31.87 | 25.52 | 43.67 | 40.82 | 39.29 |
| 7500-3500 | 15.63 | 8.93 | 7.64 | 16.74 | 9.23 |
| 13500-7500 | 2.88 | 1.41 | 0.19 | 2.28 | 0.38 |
| >13500 | 0.2 | 0.21 | 0 | 0 | 0 |

Figure 2A:
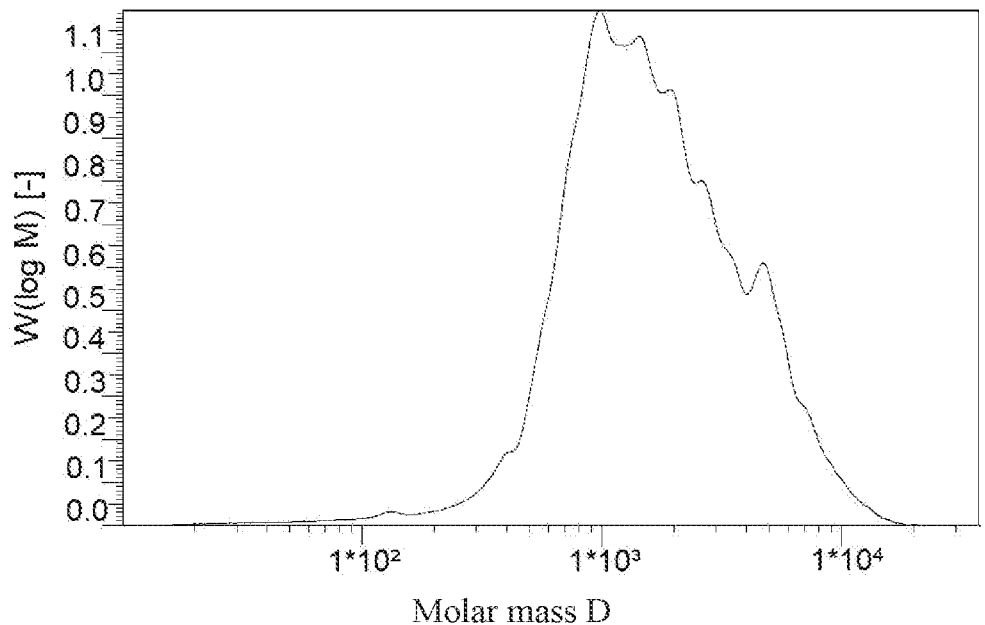
FIG. 2A shows a chromatogram of a 1% strength solution of comparative product 1. The molecular weight is plotted on the abscissa with a logarithmic scale.
Figure 2B:
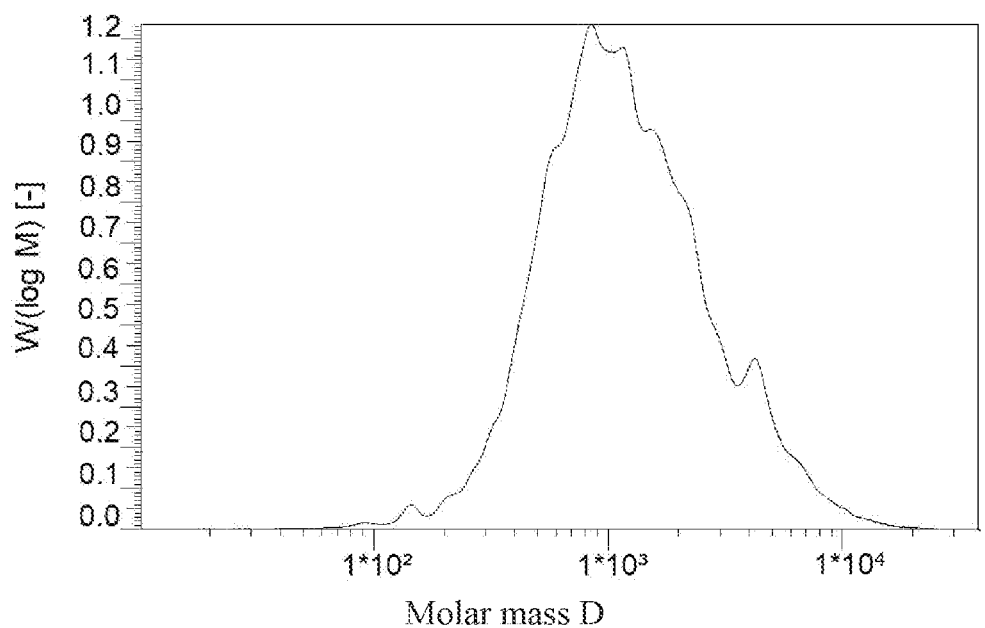
FIG. 2B shows a chromatogram of a 1% strength solution of comparative product 2. The molecular weight is plotted on the abscissa with a logarithmic scale.
Figure 3A:
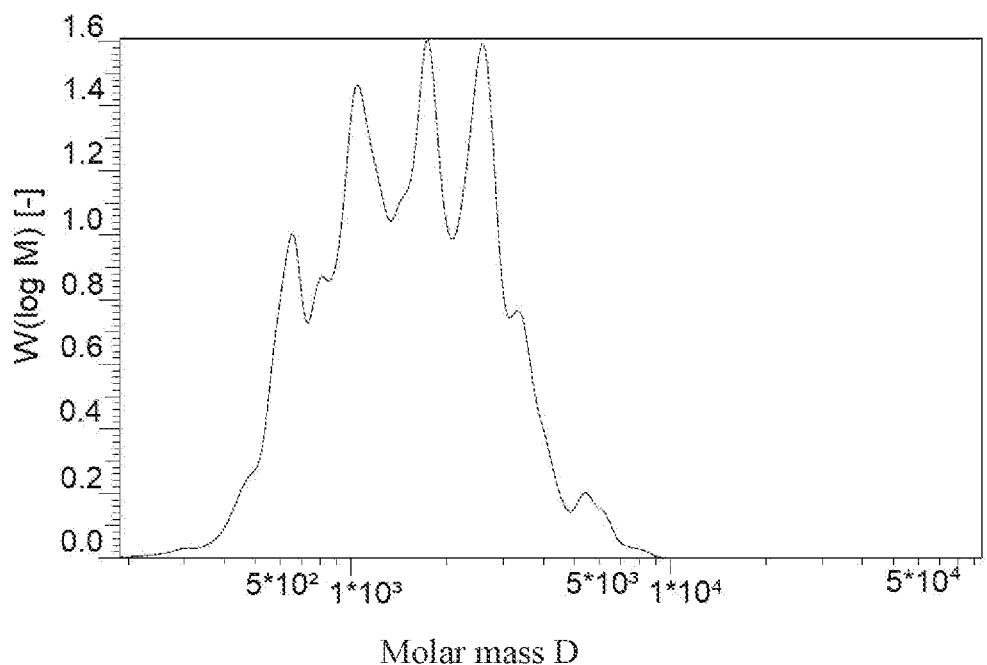
FIG. 3A shows a chromatogram of a 1% strength solution of the collagen peptide preparation according to Example 1.3. The molecular weight is plotted on the abscissa with a logarithmic scale.
Figure 3B:
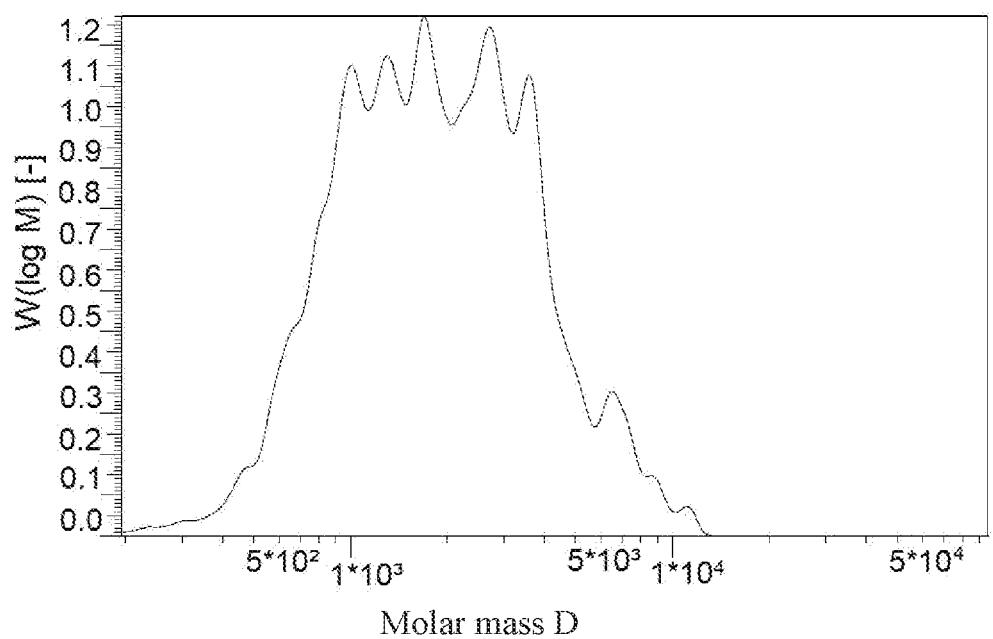
FIG. 3B shows a chromatogram of a 1% strength solution of the collagen peptide preparation according to Example 1.4. The molecular weight is plotted on the abscissa with a logarithmic scale.
Figure 4:
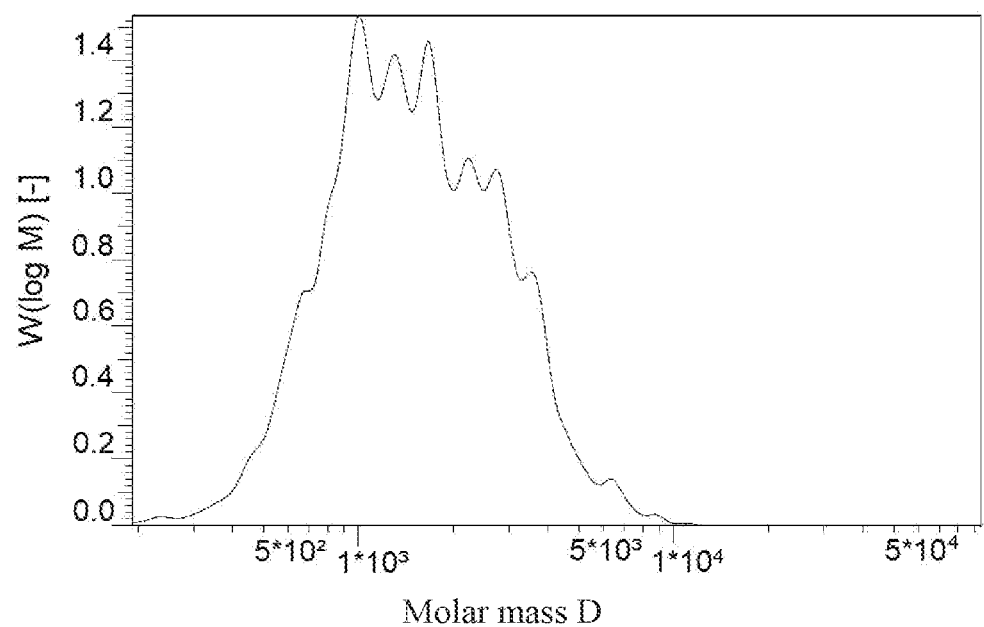
FIG. 4 shows a chromatogram of a 1% strength solution of the collagen peptide preparation according to Example 1.5. The molecular weight is plotted on the abscissa with a logarithmic scale.

Chromatograms of a 1% solution each of the comparison products and the collagen peptide preparations according to Examples 1.3 to 1.5 are shown in FIGS. 2 to 4. Due to the narrower molecular weight distribution, the lack of higher molecular weight peptides and the implementation of the hydrolysis according to the invention, the percentage of peptides<500 Da may be significantly reduced and a product having an average molecular weight of less than 2 kDa may still be achieved. At the same time, the number of peptides in the preferred size range between 1500 and 3500 Da is increased significantly. While peptides>1500 Da are classified as neutral in taste by the person skilled in the art, it is precisely the low molecular weight peptides<500 Da that contribute significantly to the bitterness of collagen peptide products.

The avoidance of the formation of such peptides is a further advantage for the production of sensory and organoleptically excellent collagen peptides classified as "neutral" tasting by the consumer. The same also applies to products having a higher average molecular weight in the range from 3 to 7 kDa.

From the above-mentioned embodiments it may be deduced that the method according to the invention and thus the use of uniform recombinant collagen fragments as starting material for the hydrolysis enables the formation of preferred individual peptides within a narrow molecular weight distribution which, depending on the hydrolysis conditions selected, has characteristic peaks, usually between 4 and 6 (FIG. 3A, FIG. 3B, FIG. 4).

The formation of these individual peptides may be specifically controlled through the choice of the starting fragment as well as the hydrolysis conditions, which is almost impossible when using animal starting material due to their inhomogeneity.

Example 2—Ex Vivo Hydroxylation of Collagen Fragments

For the post-translational modification (hydroxylation of proline residues) of collagen fragments ex vivo, a specific 4-OH prolyl hydroxylase (P4H) in the presence of the cofactors α-ketoglutarate, iron (II) ions and $O_2$ was used, the use of nonspecific hydroxylases also being conceivable. For this purpose, 8 mM of the collagen fragment in the presence of 14 mM α-ketoglutarate, 0.5 mM iron (II) sulfate and 1.5 mM L-ascorbic acid in 50 mM MES buffer (pH 6.5) and of an enzyme solution in a total volume of 1 mL were incubated while shaking (300 RPM) at 37° C. on a thermomixer for 14 to 18 hours. Alternatively, the incubation may also take place in an incubator under the aforementioned conditions.

Example 3—Osteoblast Activity (Particularly Bone Health)

To analyze the biological effectiveness of the collagen peptide preparation according to the invention in terms of maintaining bone health and the prophylaxis and treatment of bone diseases, its stimulating effect on the synthesis of matrix proteins and enzymes that play a role in the structure and mineralization of the matrix is examined via osteoblasts in vitro. This is done by determining the expression of the corresponding mRNA by means of real-time PCR and a semi-quantitative evaluation (based on a control without collagen hydrolyzate).

For this purpose, human osteoblasts are first isolated from knee joints by incubating bone material under vigorous agitation at 37° C. for 1 h in Hanks' solution, supplemented with 7 mg/ml hyaluronidase type I and III-S and 5 mg/ml pronase. The digestion is then continued at 37° C. for 3-5 h in Hanks' solution supplemented with 16 mg/ml collagenase type CLS IV. The primary osteoblasts obtained are cultivated after enzymatic digestion in Ham's F12 medium, supplemented with 10% fetal calf serum, 20 U/ml penicillin-streptomycin, 50 µg/ml partricin, 0.05 mg/ml ascorbic acid and 0.15 mg/ml glutamine. Alternatively, primary osteoblasts (Article No. C-12760; 2019) may also be obtained from PromoCell GmbH, Heidelberg, Germany for investigating the biological effectiveness. The cells are then cultivated in Ham's F12 medium, supplemented with 10% fetal calf serum, 20 U/ml penicillin-streptomycin, 50 µg/ml partricin and 0.15 mg/ml glutamine.

To investigate the biological effectiveness, monolayer cell cultures of the isolated human osteoblasts are incubated for a period of 24 hours in a medium that is supplemented with 0.5 mg/ml of the respective collagen peptide preparation. A control is incubated in each case in a medium without preparation. The respective mRNA expression is then determined.

Example 4—Fibroblast Activity (Particularly Skin Health)

Example 4.1—Stimulation of mRNA Synthesis

The stimulation of the synthesis of collagen (type 1) and the proteoglycans biglycan and versican is investigated in vitro on human dermal fibroblasts (skin cells). For this purpose, the cells are incubated for 24 hours with 0.5 mg/ml of a low molecular weight or the collagen peptide preparation according to the invention, and the expression of collagen RNA, biglycan RNA and versican RNA is then determined by real-time PCR and semi-quantitatively (based on a control without preparation).

Example 4.2—Stimulation of the Synthesis of Connective Tissue Proteins

To determine the stimulation of the synthesis of proteins of the connective tissue via the collagen peptide preparations according to the invention, primary human dermal fibroblasts after enzymatic digestion are initially cultured in HAM's F12 medium, comprising 10% FCS, 20 U/ml penicillin-streptomycin, 50 µg/ml partricin, 0.05 mg/ml ascorbic acid and 0.15 mg/ml glutamine. After reaching a confluence of 80%, the respective culture medium is replaced by a medium without collagen peptide (control) or with 0.5 mg/ml of a collagen peptide preparation to be tested, and the primary human fibroblasts are incubated in the respective medium for a period of at least 14 days, preferably 14 to 21 days, in particular 14 days. The expression of different proteins of the connective tissue may then be determined and evaluated by means of suitable assays (see, for example, Examples 6 and 7).

Example 5—Chondrocyte Activity (Particularly Cartilage Health)

For the cell cultures, porcine or human chondrocytes are isolated from cartilage tissue in a known manner and sown on culture plates at a density of approximately 350,000 cells/cm$^2$. Ham's F12 medium with 10% fetal calf serum, 10 µg/ml gentamicin and 5 µg/ml amphotericin B is used as the culture medium. As an alternative to 10 µg/ml gentamicin, 10 µg/ml penicillin-streptomycin may also be used. The cultivation took place at 37° C. in an oxygen-reduced atmosphere (5% $O_2$, 5% $CO_2$ and 90% $N_2$).

Determination of Collagen Biosynthesis:

The quantification of the collagen synthesized by the chondrocytes (essentially type II) is carried out by radioactive labeling with $^{14}$C-proline, which is incorporated into the collagen.

$^{14}$C-proline is first added to the culture medium and the chondrocytes are cultivated under these conditions until the time of the determination. In order to be able to distinguish the incorporated from non-incorporated $^{14}$C-proline during the detection, the isotope-containing culture medium is then replaced by pure culture medium for a period of 3 days. The culture medium is then discarded and the adherent cell layer is mixed with distilled water in order to destroy the cell membranes through osmotic stress and to release cytosolic, unbounded $^{14}$C-proline. The cell debris with the synthesized extracellular matrix is pelleted by centrifugation. The pellet is re-suspended in fresh distilled water and a xylene scintillation cocktail is added. The amount of synthesized collagen may then be quantified by detecting the 14C-Proline with a beta counter.

Alternatively, the quantification may be carried out using the Sircol Collagen Assay Kit (Article No. 054S5000, 2019, tebu-bio, Offenbach, Germany, or Biocolor Ltd., UK) according to manufacturer instructions (see Examples 6 and 7).

Determination of Proteoglycan Biosynthesis:

The proteoglycans synthesized by the chondrocytes are quantified by means of Alcian blue staining and photometric determination of the glycosaminoglycans (GAG), which are components of the proteoglycans.

In order to determine the GAG content in the cell culture, the culture medium is first discarded and the adherent cell layer is rinsed with PBS buffer (pH 7). The cells are then fixed in a 10% formaldehyde solution in PBS at 4° C. for 2 hours. After removing the formaldehyde, the Alcian blue staining reagent (5% Alcian blue in 3% acetic acid) is applied to the cell lawn and incubated at 4° C. overnight. Unbound Alcian blue is discarded and washed out by carefully rinsing three to four times with PBS. By adding acidic guanidine solution (8 mol/l), the GAG complexes are released from the cell layer. The amount of glycosaminoglycans may then be quantified photometrically at a wavelength of 620 nm.

Alternatively, the quantification may be carried out using the Blyscan Glycosaminoglycan Assay Kit (Article No. 054B3000, 2019, tebu-bio, Offenbach, Germany, or Biocolor Ltd., UK) according to manufacturer instructions (see Examples 6 and 7).

Example 6—Stimulation of the Synthesis of Collagen, Elastin and Proteoglycan in Primary Human Fibroblasts Via Non-Hydroxylated Collagen Peptide Preparations According to the Invention To determine the stimulation of the synthesis of collagen, elastin and proteoglycan, primary human dermal fibroblasts according to Example 4.2 were incubated for a period of at least 14 days, preferably 14 to 21 days, in particular 14 days, in a medium without collagen peptide (control 1) and in the presence of 0.5 mg/ml of a 100 kDa collagen peptide (control 2), of a collagen peptide preparation having an average molecular weight of 1.8 kDa (sample 1), of a collagen peptide preparation having an average molecular weight of 2.4 kDa (sample 2) and one of a collagen peptide preparation having an average molecular weight of 3.4 kDa (sample 3).

Example 6.1—Determination of the Stimulation of the Synthesis of Collagen

The determination of collagen synthesis by primary human dermal fibroblasts was carried out using the Sircol Collagen Assay Kit (Article No. 054S5000, 2019, tebu-bio, Offenbach, Germany, or Biocolor Ltd., UK) according to manufacturer instructions. The results of the experiment are shown in Table 2 and FIG. 5.

TABLE 2

Determination of the optical density (OD) at a wavelength of 450 nm for ascertaining the collagen synthesis according to the Sircol Collagen Assay (tebu-bio, Offenbach, Germany, or Biocolor Ltd., UK).

|  | Control 1 | Control 2 (molecular weight = 100 kDa) | Sample 1 (average molecular weight = 1.8 kDa) | Sample 2 (average molecular weight = 2.4 kDa) | Sample 3 (average molecular weight = 3.4 kDa) |
|---|---|---|---|---|---|
| Average ($OD_{450}$) | 1 | 1.01 | 1.2 | 1.24 | 1.21 |
| Standard deviation | 0 | 0.01 | 0.07 | 0.1 | 0.06 |

Example 6.2—Determination of the Stimulation of the Synthesis of Elastin

The determination of elastin synthesis via primary human dermal fibroblasts was carried out using the Fastin Elastin Assay (Article No. 054F2000, 2019, tebu-bio, Offenbach, Germany, or Biocolor Ltd., UK) according to manufacturer instructions. The results of the experiment are shown in Table 3 and FIG. 6.

TABLE 3

Determination of the optical density (OD) at a wavelength of 450 nm for ascertaining the elastin synthesis according to the Fastin Elastin Assay (tebu-bio, Offenbach, Germany, or Biocolor Ltd., UK).

|  | Control 1 | Control 2 (molecular weight = 100 kDa) | Sample 1 (average molecular weight = 1.8 kDa) | Sample 2 (average molecular weight = 2.4 kDa) | Sample 3 (average molecular weight = 3.4 kDa) |
|---|---|---|---|---|---|
| Average ($OD_{450}$) | 1 | 0.96 | 1.28 | 1.25 | 1.38 |
| Standard deviation | 0 | 0.22 | 0.13 | 0.02 | 0.3 |

Example 6.3—Determination of the Stimulation of the Synthesis of Glycosaminoglycan The determination of the synthesis of glycosaminoglycans via primary human dermal fibroblasts was carried out using the Blyscan glycosaminoglycan assay (Article No. 054B3000, 2019, tebu-bio, Offenbach, or Biocolor Ltd., UK) according to manufacturer instructions. The results of the experiment are shown in Table 4 and FIG. 7.

TABLE 4

Determination of the optical density (OD) at a wavelength of 450 nm for ascertaining the synthesis of glycosaminoglycans according to the Blyscan Glycosaminoglycan Assay (tebu-bio, Offenbach, Germany, or Biocolor Ltd., UK).

|  | Control 1 | Control 2 (molecular weight = 100 kDa) | Sample 1 (average molecular weight = 1.8 kDa) | Sample 2 (average molecular weight = 2.4 kDa) | Sample 3 (average molecular weight = 3.4 kDa) |
|---|---|---|---|---|---|
| Average ($OD_{450}$) | 1 | 1 | 1.28 | 1.26 | 1.2 |
| Standard deviation | 0 | 0.09 | 0.08 | 0.08 | 0.06 |

Example 7—Stimulation of the Synthesis of Collagen, Elastin and Proteoglycan in Primary Human Fibroblasts Via Hydroxylated Collagen Peptide Preparations According to the Invention To determine the stimulation of the synthesis of collagen, elastin and proteoglycan, primary human dermal fibroblasts according to Example 4.2 were incubated for a period of at least 14 days, preferably 14 to 21 days, in particular 14 days, in a medium without collagen peptide (control 1) and in the presence of 0.5 mg/ml of a collagen peptide preparation having an average molecular weight of 7.0 kDa (sample 4), of a collagen peptide preparation having an average molecular weight of 5.6 kDa (sample 5) and of a collagen peptide preparation having an average molecular weight of 1.3 kDa (Sample 6).

Example 7.1—Determination of the Stimulation of the Synthesis of Collagen

The determination of collagen synthesis via primary human dermal fibroblasts was carried out using the Sircol Collagen Assay Kit (Article No. Article No. 054S5000, 2019, tebu-bio, Offenbach, Germany, or Biocolor Ltd., UK) according to manufacturer instructions. The results of the experiment are shown in Table 5 and FIG. 8. The average value ascertained for the untreated control (control 1) was standardized to 1 as standard.

TABLE 5

Determination of the optical density (OD) for ascertaining the collagen synthesis according to the Sircol Collagen Assay (tebu-bio, Offenbach, Germany, or Biocolor Ltd., UK).

|  | Control 1 | Sample 4 (average molecular weight = 7.0 kDa) | Sample 5 (average molecular weight = 5.6 kDa) | Sample 6 (average molecular weight = 1.3 kDa) |
|---|---|---|---|---|
| Average | 1 | 1.35 | 1.36 | 1.39 |
| Standard deviation | 0 | 0.16 | 0.1 | 0.09 |

Example 7.2—Determination of the Stimulation of the Synthesis of Elastin

The determination of elastin synthesis by primary human dermal fibroblasts was carried out using the Fastin Elastin Assay (Article No. 054F2000, 2019, tebu-bio, Offenbach, Germany or Biocolor Ltd., UK) according to manufacturer instructions. The results of the experiment are shown in Table 6 and FIG. 9. The average value ascertained for the untreated control (control 1) was standardized to 1 as standard.

TABLE 6

Determination of the optical density (OD) for ascertaining the elastin synthesis according to the Fastin Elastin Assay (tebu-bio, Offenbach, Germany, or Biocolor Ltd., UK).

|  | Control 1 | Sample 4 (average molecular weight = 7.0 kDa) | Sample 5 (average molecular weight = 5.6 kDa) | Sample 6 (average molecular weight = 1.3 kDa) |
|---|---|---|---|---|
| Average | 1 | 1.32 | 1.33 | 1.31 |
| Standard deviation | 0 | 0.11 | 0.07 | 0.04 |

Example 7.3—Determination of the Stimulation of the Synthesis of Glycosaminoglycan The determination of the synthesis of glycosaminoglycans via primary human dermal fibroblasts was carried out using the Blyscan glycosaminoglycan assay (Article No. 054B3000, 2019, tebu-bio, Offenbach, or Biocolor Ltd., UK) according to manufacturer instructions. The results of the experiment are shown in Table 7 and FIG. 10. The average value ascertained for the untreated control (control 1) was standardized to 1 as standard.

TABLE 7

Determination of the optical density (OD) for ascertaining the synthesis of glycosaminoglycans according to the Blyscan Glycosaminoglycan Assays (tebu-bio, Offenbach, Germany, or Biocolor Ltd., UK).

|  | Control 1 | Sample 4 (average molecular weight = 7.0 kDa) | Sample 5 (average molecular weight = 5.6 kDa) | Sample 6 (average molecular weight = 1.3 kDa) |
|---|---|---|---|---|
| Average | 1 | 1.37 | 1.41 | 1.40 |
| Standard deviation | 0 | 0.15 | 0.11 | 0.12 |

The invention claimed is:

1. A method for producing a collagen peptide preparation, comprising:
   a) expressing, from a coding nucleotide sequence, a collagen peptide having a molecular weight in a range from 8 to 100 kDa, and
   b) enzymatically hydrolyzing the expressed collagen peptide under conditions to produce a collagen peptide preparation comprising hydrolyzed collagen peptides having an average molecular weight of 1 to 5 kDa, wherein
   no more than 5.5 wt.-% of the hydrolyzed collagen peptides have a molecular weight less than 500 Da,
   no more than 2.8 wt.-% of the hydrolyzed collagen peptides have a molecular weight between 7500 Da and 13500 Da, and
   from 35 to 60 wt.-% of the hydrolyzed collagen peptides have a molecular weight between 1500 Da and 3500 Da.

2. The method according to claim 1, wherein the collagen peptide is expressed in a host cell selected from the group consisting of bacterial cell, yeast cell, fungal cell, mammalian cell, insect cell and plant cell.

3. The method according to claim 2, wherein the host cell is capable of hydroxylating proline residues, lysine residues or proline residues and lysine residues of the expressed collagen peptide.

4. The method according to claim 3, wherein the host cell comprises a polynucleotide sequence that encodes a prolyl 4-hydroxylase.

5. The method according to claim 3, wherein the host cell comprises a polynucleotide sequence that encodes a lysyl hydroxylase.

6. The method according to claim 2, wherein the host cell is incapable of causing hydroxylation of proline residues, lysine residues or proline and lysine residues of the expressed collagen peptide.

7. The method according to claim 6, wherein the expressed collagen peptide is hydroxylated before the hydrolysis.

8. The method according to claim 6, wherein the expressed collagen peptide is further hydroxylated after the hydrolysis.

9. The method according to claim 1, wherein the collagen peptide is a collagen peptide of a vertebrate, a mammal, a bird, a fish, an amphibian, a reptile, or an invertebrate animal.

10. The method according to claim 1, wherein the hydrolyzed collagen peptides have a molecular weight in a range 0.1 to 13.5 kDa.

11. A method for improving a skin, for accelerating the growth or reducing the fragility of nails, for improving hair, for increasing the number or activity of mitochondria, or for improving endurance or mental performance of a subject, comprising administering the subject an effective amount of hydrolyzed collagen peptides producible by the method of claim 1.

12. A food supplement comprising hydrolyzed collagen peptides producible according to claim 1 and at least one food-acceptable additive.

13. A cosmetic product comprising hydrolyzed collagen peptides producible according to claim 1 and at least one skin-compatible additive.

\* \* \* \* \*